(12) United States Patent
Kodama et al.

(10) Patent No.: US 7,893,008 B2
(45) Date of Patent: Feb. 22, 2011

(54) OLIGONUCLEOTIDES, ARRAYS THEREOF FOR DETECTING MICROORGANISMS, AND AN APPARATUS, A METHOD AND A KIT FOR DETECTING MICROORGANISMS

(75) Inventors: Yukiko Kodama, Osaka (JP); Kazushige Hatanaka, Kyoto (JP); Koichi Tanaka, Osaka (JP); Hiroko Nakagawa, Chiba (JP); Shogo Moriya, Chiba (JP); Kaoru Osano, Chiba (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 3 days.

(21) Appl. No.: 11/990,484

(22) PCT Filed: Aug. 16, 2006

(86) PCT No.: PCT/JP2006/316440

§ 371 (c)(1),
(2), (4) Date: May 22, 2008

(87) PCT Pub. No.: WO2007/021027

PCT Pub. Date: Feb. 22, 2007

(65) Prior Publication Data
US 2009/0048118 A1    Feb. 19, 2009

(30) Foreign Application Priority Data
Aug. 16, 2005   (JP) .............................. 2005-236174

(51) Int. Cl.
*C40B 30/04*   (2006.01)
*C40B 40/08*   (2006.01)
*C07H 21/04*   (2006.01)
*C12M 1/00*    (2006.01)
*C12Q 1/68*    (2006.01)

(52) U.S. Cl. .......................... 506/16; 506/9; 435/287.2; 435/6; 536/24.33

(58) Field of Classification Search ...................... None
See application file for complete search history.

(56) References Cited

U.S. PATENT DOCUMENTS

2004/0166492 A1 *   8/2004   Engel et al. .................... 435/6

FOREIGN PATENT DOCUMENTS

JP         07-289295         11/1995

OTHER PUBLICATIONS

Egli (Jan. 26, 1999) GenBank accession No. AF043503 downloaded Mar. 28, 2010 from http://www.ncbi.nlm.nih.gov/nuccore/4191308 Entrez Nucleotide section pp. 1 to 2.*

(Continued)

*Primary Examiner*—Jeffrey S Lundgren
*Assistant Examiner*—Christian Boesen
(74) *Attorney, Agent, or Firm*—Drinker Biddle & Reath LLP

(57) ABSTRACT

The present invention relates to an instrument, a method and a kit for detecting a microorganism contaminating a subject test sample, which enables one to quickly and accurately identify the microorganism with an easy operation. The instrument for detecting a microorganism according to the present invention relates to a microarray type instrument in which oligonucleotides prepared based on nucleotide sequences specific to the species and genus to which the subject microorganism belongs have been immobilized onto a surface of a substrate. Based on the presence or absence of hybridization of the probes prepared from the test sample with the oligonucleotides immobilized onto the surface of the substrate, the present invention makes it possible to detect and/or identify the microorganism in the test sample easily, quickly and accurately.

19 Claims, 1 Drawing Sheet

OTHER PUBLICATIONS

Egli (Jan. 26, 1999) GenBank accession No. AF043509 downloaded Mar. 28, 2010 from http://www.ncbi.nlm.nih.gov/nuccore/4191314 Entrez Nucleotide section pp. 1 to 2.*

Cocolin (Mar. 2004) Applied and Environmental Microbiology vol. 70 pp. 1347 to 1355.*

Fukushimi (Jun. 2003) Journal of Clinical Microbiology vol. 41 pp. 2605 to 2615.*

O. Vinnere et al., "A new plant pathogenic sterile white basidiomycete from Australia," European Journal of Plant Pathology, vol. 112, No. 1, May 2005, pp. 63-77, XP002404779 ISSN: 0929-1873.

M. Nakamura et al., "Development of the DNA Micro Array for Identification of Infectious Disease Causative Bacteria in Human," Abstracts of the General Meeting of the American Society for Microbiology, The Society, Washington, DC, US, vol. 103, May 18, 2003, p. ABSTRNOC219, XP008047725 ISSN: 1060-2011.

J. Li et al., "A DNA Microarray-Based Method for Simultaneous Detection and Identification of Six Bacterial Pathogens in a Single Sample," Abstracts of the General Meeting of the American Society for Microbiology, The Society, Washington, DC, US, vol. 101, May 23, 2001, p. 575, XP009014436 ISSN: 1060-2011.

International Search Report issued on Jan. 11, 2007 in International PCT Application No. PCT/JP2006/316440 filed Aug. 16, 2006.

* cited by examiner

OLIGONUCLEOTIDES, ARRAYS THEREOF FOR DETECTING MICROORGANISMS, AND AN APPARATUS, A METHOD AND A KIT FOR DETECTING MICROORGANISMS

CROSS REFERENCE TO RELATED APPLICATIONS

This application is the National Stage of International Application No. PCT/JP2006/316440 filed Aug. 16, 2006, and claims benefit of Japanese Application No. 2005-236174 filed Aug. 16, 2005, both of which are herein incorporated by reference in their entirety.

TECHNICAL FIELD

The present invention relates to oligonucleotides, arrays thereof for detecting microorganisms, and an apparatus, a method and a kit for detecting microorganisms.

BACKGROUND ART

Contamination of food by harmful microorganisms causes deterioration in quality of the food. For example, contamination of malt alcoholic beverages by harmful microorganisms causes turbidity and/or degradation of flavor of the beverages. Moreover, contamination of beer by *Brettanomyces (Dekkera), Candida, Pichia, Hanseniaspora, Saccharomyces* with exception of those for brewery yeasts, and the like, deteriorates the quality of the beer, causing turbidity and/or off-flavor. Currently, the most commonly used method for detecting the harmful microorganisms in beer is a method that comprises filtering beer of interest through a membrane filter, thereafter culturing the beer and detecting a colony that has grown.

Further, in order to determine whether the colony is the one that corresponds to the harmful microorganisms, a method that comprises performing PCR with a primer specific to the harmful organisms using a DNA extracted from the colony as a template, and determining whether a PCR product is obtained by electrophoresis is used (see, for example, Japanese Laid-open Patent Publication No. 7-289295). However, this method is extremely cumbersome and time consuming because a multiple runs of PCR must be performed for each microorganism using a large numbers of primers. A large numbers of primers may be used as a mixture in a single tube for amplification reactions in order to shorten the time required for the method. However, the number of available primers is limited and it is difficult to perform precise determination provided there is trace amount of specimen.

In order to solve these problems, there have been proposed different methods of identifying microorganisms. In these methods, primers are designed in such a manner that only a portion of a gene that commonly exists across different microorganisms and that contains species-specific sequences is amplified. After the amplification, the amplified product is excised by restriction enzymes that recognize the species-specific sequences, and microorganisms are identified based on the band size obtained by electrophoresis. However, it is not necessarily the case that such restriction enzymes are available for all species of microorganisms to be tested. Further, since the methods require the highly complicated procedure of excising the amplified product with several different kinds of restriction enzymes for electrophoresis, the methods are also problematic in terms of speed and readiness.

Further, a method, in which a species-specific sequence is used as a probe, and the presence or absence of a complementary sequence in the tested DNA or RNA is determined by hybridization, has been used to solve these problems.

DISCLOSURE OF INVENTION

However, the methods employing hybridization also pose a problem in that cross-hybridization with other species often occurs between closely related species having a high level of DNA homology. As this is often the case, it is difficult to accurately identify microorganisms.

Therefore, a method for identifying a microorganism that makes it possible to determine the presence of a specific strain of microorganisms more accurately and more easily is desired.

Specifically, a nucleic acid probe that can be used for the method described above with specificity and without the problem of cross-hybridization is desired.

The present inventors made exhaustive investigations and as a result, found sequences specific to certain genus or species in the nucleotide sequence corresponding to the ITS region (a spacer region between the 18S ribosomal RNA gene and the 25S ribosomal RNA gene of a microorganism) of typical contaminating microorganisms for malt alcoholic beverages, and found that it is possible to quickly and precisely detect and/or identify a microorganism of interest in a test sample using the oligonucleotide based on the nucleotide sequence as a probe, and has come to accomplish the present invention.

That is, the present invention provides an oligonucleotide, an oligonucleotide array for detecting the presence of a microorganism in a test sample, an instrument, a kit for detecting a microorganism comprising such an array, and a method for detecting the presence of a microorganism in a test sample, as follows:

[1] An oligonucleotide comprising any one of the nucleic acid sequences of SEQ ID NOs: 1-64.

[1a] An oligonucleotide consisting of any one of the nucleic acid sequences of SEQ ID NOs: 1-64.

[2] The oligonucleotide according to [1] or [1a] for use as a probe for detecting the presence of a microorganism in a test sample.

[2a] The oligonucleotide according to [2], wherein said test sample is food.

[2b] The oligonucleotide according to [2], wherein said test sample is a malt alcoholic beverage.

[3] An oligonucleotide having a nucleic acid sequence comprising either one of the sequences of SEQ ID NOs.: 1-64, and being capable of hybridizing to a complementary sequence of a nucleic acid sequence of a microorganism belonging to the group selected from the following groups (i) to (vii); or to a complementary sequence of a nucleic acid sequence of a microorganism belonging to the group each of which consists of a plurality of microorganisms selected from the following groups (i) to (vii):

(i) a microorganism belonging to *Brettanomyces (Dekkera) bruxellensis;*

(ii) a microorganism belonging to *Brettanomyces (Dekkera) anomala;*

(iii) a microorganism belonging to *Saccharomyces cerevisiae, Saccharomyces diastaticus, Saccharomyces pastorianus,* or *Saccharomyces bayanus;*

(iv) a microorganism belonging to *Pichia anomala;*

(v) a microorganism belonging to *Hanseniaspora uvarum* or *Hanseniaspora guilliermondii;*

(vi) a microorganism belonging to *Candida valida* or *Pichia membranaefaciens;* and (vii) a microorganism belonging to *Brettanomyces (Dekkera) bruxellensis* or *Brettanomyces (Dekkera) anomala*.

[4] An oligonucleotide array for detecting the presence of a microorganism in a test sample, comprising at least one oligonucleotide comprising any one of nucleic acid sequences selected from the group consisting of the nucleic acid sequences of SEQ ID NOs.: 1-64, wherein said oligonucleotide is immobilized to a support.

[4a] An oligonucleotide array for detecting the presence of a microorganism in a test sample, comprising at least one oligonucleotide consisting of any one of nucleotide sequences selected from the group consisting of the nucleic acid sequences of SEQ ID NOs.: 1-64, wherein said oligonucleotide is immobilized to a support.

[5] An oligonucleotide array for detecting the presence of a microorganism in a test sample, comprising any one of the oligonucleotides or any combination of the oligonucleotides of the following (A) to (G):

(A) at least one oligonucleotide comprising any one of the nucleic acid sequences selected from the group consisting of the nucleic acid sequences of SEQ ID NOs.: 1-6, 8 and 10-14;

(B) at least one oligonucleotide comprising any one of the nucleic acid sequences selected from the group consisting of the nucleic acid sequences of SEQ ID NOs. 15-22 and 25-29;

(C) at least one oligonucleotide comprising any one of the nucleic acid sequences selected from the group consisting of the nucleic acid sequences of SEQ ID NOs.: 30-43;

(D) at least one oligonucleotide comprising any one of the nucleic acid sequences selected from the group consisting of the nucleic acid sequences of SEQ ID NOs.: 44-52;

(E) at least one oligonucleotide comprising any one of the nucleic acid sequences selected from the group consisting of the nucleic acid sequences of SEQ ID NOs.: 53-56;

(F) at least one oligonucleotide comprising any one of the nucleic acid sequences selected from the group consisting of the nucleic acid sequences of SEQ ID NOs.: 57-64; or (G) at least one oligonucleotide comprising any one of the nucleic acid sequences selected from the group consisting of the nucleic acid sequences of SEQ ID NOs.: 7, 9, 23 and 24, wherein said oligonucleotide is immobilized to a support.

[5a] An oligonucleotide array for detecting the presence of a microorganism in a test sample, consisting any one of the oligonucleotides or any combination of the oligonucleotides of the following (A) to (G):

(A) at least one oligonucleotide consisting any one of the nucleic acid sequences selected from the group consisting of the nucleic acid sequences of SEQ ID NOs.: 1-6, 8 and 10-14;

(B) at least one oligonucleotide consisting any one of the nucleic acid sequences selected from the group consisting of the nucleic acid sequences of SEQ ID NOs.: 15-22 and 25-29;

(C) at least one oligonucleotide consisting any one of the nucleic acid sequences selected from the group consisting of the nucleic acid sequences of SEQ ID NOs.: 30-43, (D) at least one oligonucleotide consisting any one of the nucleic acid sequences selected from the group consisting of the nucleic acid sequences of SEQ ID NOs.: 44-52;

(E) at least one oligonucleotide consisting any one of the nucleic acid sequences selected from the group consisting of the nucleic acid sequences of SEQ ID NOs.: 53-56;

(F) at least one oligonucleotide consisting any one of the nucleic acid sequences selected from the group consisting of the nucleic acid sequences of SEQ ID NOs.: 57-64; or (G) at least one oligonucleotide consisting any one of the nucleic acid sequences selected from the group consisting of the nucleic acid sequences of SEQ ID NOs.: 7, 9, 23 and 24, wherein said oligonucleotide is immobilized to a support.

[6] The oligonucleotide array according to [5] comprising at least the oligonucleotide of the above (A).

[7] The oligonucleotide array according to [6], wherein said microorganism belongs to *Brettanomyces (Dekkera) bruxellensis*.

[8] The oligonucleotide array according to [5] comprising at least the oligonucleotide of the above (C).

[9] The oligonucleotide array according to [8], wherein said microorganism belongs to *Brettanomyces (Dekkera) anomala*.

[10] The oligonucleotide array according to [5] comprising at least the oligonucleotide of the above (C).

[11] The oligonucleotide array according to [10], wherein said microorganism belongs to *Saccharomyces cerevisiae, Saccharomyces diastaticus, Saccharomyces pastorianus*, or *Saccharomyces bayanus*.

[12] The oligonucleotide array according to [5] comprising at least the oligonucleotide of the above (D).

[13] The oligonucleotide array according to [12], wherein said microorganism belongs to *Pichia anomala*.

[14] The oligonucleotide array according to [5] comprising at least the oligonucleotide of the above (E).

[15] The oligonucleotide array according to [14], wherein said microorganism belongs to *Hanseniaspora uvarum* or *Hanseniaspora guilliermondii*.

[16] The oligonucleotide array according to [5] comprising at least the oligonucleotide of the above (F).

[17] The oligonucleotide array according to [16], wherein said microorganism belongs to *Candida valida* or *Pichia membranaefaciens*.

[18] The oligonucleotide array according to [5] comprising at least the oligonucleotide of the above (G).

[19] The oligonucleotide array according to [18], wherein said microorganism belongs to *Brettanomyces (Dekkera) bruxellensis* or *Brettanomyces (Dekkera) anomala*.

[20] The oligonucleotide array according to any one of [4] to [19], wherein said test sample is food.

[20a] The oligonucleotide array according to any one of [4] to [19], wherein said test sample is malt alcoholic beverage.

[21] An instrument for detecting and/or identifying that a microorganism in a test sample belongs to any one or more of groups of a microorganism selected from the following groups of microorganisms (i) to (vii):

(i) a microorganism belonging to *Brettanomyces (Dekkera) bruxellensis*;

(ii) a microorganism belonging to *Brettanomyces (Dekkera) anomala*;

(iii) a microorganism belonging to *Saccharomyces cerevisiae, Saccharomyces diastaticus, Saccharomyces pastorianus*, or *Saccharomyces bayanus*;

(iv) a microorganism belonging to *Pichia anomala*;

(v) a microorganism belonging to *Hanseniaspora uvarum* or *Hanseniaspora guilliermondii*;

(vi) a microorganism belonging to *Candida valida* or *Pichia membranaefaciens*; and (vii) a microorganism belonging to *Brettanomyces (Dekkera) bruxellensis* or *Brettanomyces (Dekkera) anomala*, wherein said instrument comprises a support to which at least one oligonucleotide that is capable of specifically hybridizing to a complementary strand of the nucleic acid of the microorganism that belongs to the selected group is immobilized, or at least two oligonucleotides that are capable of specifically hybridizing to the complementary strand of the nucleic acid of the microorganism that belongs to either of the selected plurality of the groups are immobilized.

[22] The instrument according to [21], wherein said oligonucleotide capable of specifically hybridizing to the complementary strand of the nucleic acid of the microorganism that belongs to the above group (i) is an oligonucleotide comprising any of the nucleic acid sequence selected from the group consisting of the nucleic acid sequences of SEQ ID NOs.: 1-6, 8, and 10-14.

[22a] The instrument according to [21], wherein said oligonucleotide capable of specifically hybridizing to the complementary strand of the nucleic acid of the microorganism that belongs to the above group (i) is an oligonucleotide consisting of any of the nucleic acid sequence selected from the group consisting of the nucleic acid sequences of SEQ ID NOs.: 1-6, 8, and 10-14.

[23] The instrument according to [21], wherein said oligonucleotide capable of specifically hybridizing to the complementary strand of the nucleic acid of the microorganism that belongs to the above group (ii) is an oligonucleotide comprising any of the nucleic acid sequence selected from the group consisting of the nucleic acid sequences of SEQ ID NOs.: 15-22 and 25-29.

[23a] The instrument according to [21], wherein said oligonucleotide capable of specifically hybridizing to the complementary strand of the nucleic acid of the microorganism that belongs to the above group (ii) is an oligonucleotide consisting of any of the nucleic acid sequence selected from the group consisting of the nucleic acid sequences of SEQ ID NOs.: 15-22 and 25-29.

[24] The instrument according to [21], wherein said oligonucleotide capable of specifically hybridizing to the complementary strand of the nucleic acid of the microorganism that belongs to the above group (iii) is an oligonucleotide comprising any of the nucleic acid sequence selected from the group consisting of the nucleic acid sequences of SEQ ID NOs.: 30-43.

[24a] The instrument according to [21], wherein said oligonucleotide capable of specifically hybridizing to the complementary strand of the nucleic acid of the microorganism that belongs to the above group (iii) is an oligonucleotide consisting of any of the nucleic acid sequence selected from the group consisting of the nucleic acid sequences of SEQ ID NOs.: 30-43.

[25] The instrument according to [21], wherein said oligonucleotide capable of specifically hybridizing to the complementary strand of the nucleic acid of the microorganism that belongs to the above group (iv) is an oligonucleotide comprising any of the nucleic acid sequence selected from the group consisting of the nucleic acid sequences of SEQ ID NOs.: 44-52.

[25a] The instrument according to [21], wherein said oligonucleotide capable of specifically hybridizing to the complementary strand of the nucleic acid of the microorganism that belongs to the above group (iv) is an oligonucleotide consisting of any of the nucleic acid sequence selected from the group consisting of the nucleic acid sequences of SEQ ID NOs.: 44-52.

[26] The instrument according to [21], wherein said oligonucleotide capable of specifically hybridizing to the complementary strand of the nucleic acid of the microorganism that belongs to the above group (v) is an oligonucleotide comprising any of the nucleic acid sequence selected from the group consisting of the nucleic acid sequences of SEQ ID NOs.: 53-56.

[26a] The instrument according to [21], wherein said oligonucleotide capable of specifically hybridizing to the complementary strand of the nucleic acid of the microorganism that belongs to the above group (v) is an oligonucleotide consisting of any of the nucleic acid sequence selected from the group consisting of the nucleic acid sequences of SEQ ID NOs.: 53-56.

[27] The instrument according to [21], wherein said oligonucleotide capable of specifically hybridizing to the complementary strand of the nucleic acid of the microorganism that belongs to the above group (vi) is an oligonucleotide comprising any of the nucleic acid sequence selected from the group consisting of the nucleic acid sequences of SEQ ID NOs.: 57-64.

[27a] The instrument according to [21], wherein said oligonucleotide capable of specifically hybridizing to the complementary strand of the nucleic acid of the microorganism that belongs to the above group (vi) is an oligonucleotide consisting of any of the nucleic acid sequence selected from the group consisting of the nucleic acid sequences of SEQ ID NOs.: 57-64.

[28] The instrument according to [21], wherein said oligonucleotide capable of specifically hybridizing to the complementary strand of the nucleic acid of the microorganism that belongs to the above group (vii) is an oligonucleotide comprising any of the nucleic acid sequence selected from the group consisting of the nucleic acid sequences of SEQ ID NOs.: 7, 9, 23, and 24.

[28a] The instrument according to [21], wherein said oligonucleotide capable of specifically hybridizing to the complementary strand of the nucleic acid of the microorganism that belongs to the above group (vii) is an oligonucleotide consisting of any of the nucleic acid sequence selected from the group consisting of the nucleic acid sequences of SEQ ID NOs.: 7, 9, 23, and 24.

[29] The instrument according to any one of [21] to [28a], wherein said support has carbodiimide group or an isocyanate group on the surface, and wherein said instrument is characterized in that said nucleotide is immobilized to the support through a covalent bonding formed between the carbodiimide group or the isocyanate group and the oligonucleotide or a linker attached to the terminal of the oligonucleotide as a result of reaction thereof.

[30] A method for detecting a microorganism in a test sample, identifying a group to which a microorganism in a test sample belongs, or detecting a microorganism in a test sample and identifying a group to which said microorganism belongs, comprising:

preparing a nucleic acid of a microorganism that is in a test sample;

preparing a labeled probe using said nucleic acid as a template;

hybridizing said labeled probe with the oligonucleotide immobilized to a surface of a support using the oligonucleotide according to any one of [1] to [3], the oligonucleotide array according to any one of [4] to [20], or the instrument according to any one of [21] to [29]; and detecting signals derived from said hybridization.

[31] The method according to [30] wherein said test sample is food.

[31a] The method according to [30], wherein said test sample is malt alcoholic beverage.

[32] A kit for detecting a microorganism for performing the method according to any one of [30] to [31a], comprising the oligonucleotide according to any one of [1] to [3], an array according to any one of [4] to [20], or the instrument according to any one of [21] to [29].

[33] The kit for according to [32], further comprising a reagent for use in the steps of said hybridization and said detection of the signals

[34] The kit according to [32] or [33] further comprising a reagent for use in the steps of the preparation of the probe and/or the preparation of a nucleic acid.

According to the present invention, there is provided an oligonucleotide probe that makes it possible to minimize the problem of cross-hybridization in the method for detecting and/or identifying a microorganism in a test sample.

According to the oligonucleotide array or the instrument for detecting a microorganism according to the present invention, detection and/or identification of a microorganism in a test sample is performed by conducting hybridization of an oligonucleotide prepared based on a nucleotide sequence specific to the genus or the species to which the subject microorganism belongs with a nucleic acid derived from the test sample such that a precise and simple detection and/or identification of a microorganism can be made.

In addition, an array that comprises a plurality of oligonucleotides based on nucleotide sequences specific to the species or the genus of the microorganisms is used such that a exhaustive detection can be made.

Furthermore, the kit according to the present invention comprises the oligonucleotide array or the instrument for detecting a microorganism as well as a reagent required for the detection such that an improved operability is provided and the detection and/or identification of a microorganism is much easier than previous.

BEST MODE FOR CARRYING OUT THE INVENTION

Figure 1:
FIG. 1 shows (A) an arrangement of the oligonucleotides immobilized to a substrate of the microorganism detection instrument according to the present invention, which were used in the Example; and (B) the result of detection of *Brettanomyces (Dekkera) bruxellensis* using the microorganism detection instrument according to the present invention.

In one aspect of the present invention, there is provided an oligonucleotide comprising any one of the nucleic acid sequences of SEQ ID NOs.: 1-64 (see Table 1-1 and Table 1-2). These oligonucleotides can be used as a probe for detecting the presence of a microorganism in a test sample. The test sample may be, preferably, food, and more preferably, malt alcoholic beverage.

The microorganisms that can be detected using the oligonucleotide according to the present invention are (i) a microorganism belonging to *Brettanomyces (Dekkera) bruxellensis*; (ii) a microorganism belonging to *Brettanomyces (Dekkera) anomala*; (iii) a microorganism belonging to *Saccharomyces cerevisiae, Saccharomyces diastaticus, Saccharomyces pastorianus*, or *Saccharomyces bayanus*; (iv) a microorganism belonging to *Pichia anomala*; (v) a microorganism belonging to *Hanseniaspora uvarum* or *Hanseniaspora guilliermondii*; (vi) a microorganism belonging to *Candida valida* or *Pichia membranaefaciens*; and (vii) a microorganism belonging to *Brettanomyces (Dekkera) bruxellensis* or *Brettanomyces (Dekkera) anomala*.

In another aspect of the present invention, there is provided an oligonucleotide array for detecting the presence of a microorganism in a test sample. This oligonucleotide array comprises at least one oligonucleotide comprising any one of the nucleic acid sequence selected from the group consisting of the nucleic acid sequences of SEQ ID NOs.: 1-64, wherein the oligonucleotide is immobilized to a support.

In the present invention, the oligonucleotides used as a probe for detecting and/or identifying a microorganism in a test sample can be divided into several groups according to the species or the genus as shown below. In the oligonucleotide array or the instrument for detecting a microorganism according to the present invention, at least one of the oligonucleotides shown below is immobilized to the surface of the support.

(A) An oligonucleotide based on a nucleotide sequence, which corresponds to the ITS region of a microorganism belonging to *Brettanomyces (Dekkera) bruxellensis*, and which is specific to the same species, wherein said oligonucleotide comprises any of the nucleotide sequence as shown in SEQ ID NOs.: 1-6, 8, and 10-14.

(B) An oligonucleotide based on a nucleotide sequence, which corresponds to the ITS region of a microorganism belonging to *Brettanomyces (Dekkera) anomala*, and which is specific to the same species, wherein said oligonucleotide comprises any of the nucleotide sequence as shown in SEQ ID NOs.: 15-22 and 25-29.

(C) An oligonucleotide based on a nucleotide sequence, which corresponds to the ITS region of a microorganism belonging to *Saccharomyces cerevisiae, Saccharomyces diastaticus, Saccharomyces pastorianus*, or *Saccharomyces bayanus*, and which is specific to the same species, wherein said oligonucleotide comprises any of the nucleotide sequence as shown in SEQ ID NOs.: 30-43.

(D) An oligonucleotide based on a nucleotide sequence, which corresponds to the ITS region of a microorganism belonging to *Pichia anomala*, and which is specific to the same species, wherein said oligonucleotide comprises any of the nucleotide sequence as shown in SEQ ID NOs.: 44-52.

(E) An oligonucleotide based on a nucleotide sequence, which corresponds to the ITS region of a microorganism belonging to *Hanseniaspora uvarum* or *Hanseniaspora Guilliermondii*, and which is specific to the same species, wherein said oligonucleotide comprises any of the nucleotide sequence as shown in SEQ ID NOs.: 53-56.

(F) An oligonucleotide based on a nucleotide sequence, which corresponds to the ITS region of a microorganism belonging to *Candida valida* or *Pichia membranaefaciens*, and which is specific to the same species, wherein said oligonucleotide comprises any of the nucleotide sequence as shown in SEQ ID NOs.: 57-64.

Contaminating microbes in food, especially malt alcoholic beverages (beer), miscellaneous liquors (low-malt beer), liqueur, low alcoholic beverages (for example, malt alcoholic beverages with alcohol content of less than 1%, beer-test beverages) can be detected and/or identified using the oligonucleotide array or the instrument for detecting a microorganism of the present invention, wherein the oligonucleotide as described in any of (A) to (F) above is immobilized to a surface of a support (such as a substrate).

In addition to the above-described oligonucleotides, the oligonucleotide as described below as (G) can also be immobilized to a surface of a substrate to make an oligonucleotide array or an instrument for detecting a microorganism of the present invention, which can be then used to exhaustively detect and/or identify the contaminating microbes in food.

(G) An oligonucleotide based on a nucleotide sequence, which corresponds to the ITS region of a microorganism belonging to *Brettanomyces (Dekkera) bruxellensis* or *Brettanomyces (Dekkera) anomala*, and which is specific to the same species, wherein said oligonucleotide comprises any of the nucleotide sequence as shown in SEQ ID NOs.: 7, 9, 23 and 24.

Table 1-1 and Table 1-2 show the sequences as represented by SEQ ID NOs.: 1-64, and the names of oligonucleotides which are named after corresponding microorganisms. Note that Table 1-3 shows, as described in more detail below, the sequences of control oligonucleotides used in the present invention.

TABLE 1-1

| SEQ ID NO. | NAME OF OLIGO | SEQUENCE |
|---|---|---|
| 1 | Dbru1 | AAGGATAAAAATACATTAAATT |
| 2 | Dbru1-2 | GGATAAAAATACATTAAATT |
| 3 | Dbru2 | GCAGACACGTGGATAAG |
| 4 | Dbru3 | GGATAATGATTTAAGGTTTC |
| 5 | Dbru3-2 | TGATTTAAGGTTTCGG |
| 6 | Dbru3-3 | TGAGGGGATAATGATTT |
| 7 | Dbru4 | GGTTTCGGCCGTTCATT |
| 8 | Dbru4-2 | GTTTCGGCCGTTCATT |
| 9 | Dbru4-3 | GGTTTCGGCCGTTCAT |
| 10 | Dbru5 | ACACGAGGGTGTTTTCT |
| 11 | Dbru5-2 | CACGAGGGTGTTTTCT |
| 12 | Dbru5-3 | ACACGAGGGTGTTTTC |
| 13 | Dbru6 | CCTTCTCACTATTTAGTG |
| 14 | Dbru6-2 | CCTTCTCACTATTTAGT |
| 15 | Dano1 | AGAAACACATGTATGAGG |
| 16 | Dano1-2 | GAGGAAATTATAGGGAG |
| 17 | Dano2 | TAAAACACGCAAATATA |
| 18 | Dano2-2 | CCATATAAAACACGCAA |
| 19 | Dano3 | CTCACTTCTCTGGAGTG |
| 20 | Dano3-2 | CTGGAGTGGTTATGAGA |
| 21 | Dano4 | CGGTAGTGTTTTCTTGA |
| 22 | Dano4-2 | GCGGTAGTGTTTTCTTGAA |
| 23 | Dano5 | ACAAGGTTTCGGCCG |
| 24 | Dano5-2 | ACAAGGTTTCGGCC |
| 25 | Dano5-3 | ACAAGGTTTCGGC |
| 26 | Dano5-4 | ACAAGGTTTCGG |
| 27 | Dano6 | GGGAGTATACTGGGAGG |
| 25 | Dano6-2 | CGGTGGGAGTATACTG |
| 29 | Dano6-3 | GGGAGTATACTGGGAG |
| 30 | Sac1 | TATTCCAAACGGTGAGA |
| 31 | Sac1-2 | GTGAGAGATTTCTGTGCT |
| 32 | Sac2 | TGTGGAGTTTTCATATC |
| 33 | Sac2-2 | TTTCATATCTTTGCAAC |
| 34 | Sac3 | TTTGGGCATTCGAGCA |

TABLE 1-1-continued

| SEQ ID NO. | NAME OF OLIGO | SEQUENCE |
|---|---|---|
| 35 | Sac3-2 | CTTTGGGCAITCGAG |
| 36 | Sac3-3 | GGGCATTCGAGCA |
| 37 | Sac3-4 | GCATTCGAGCAATCG |
| 38 | Sac3-5 | GGCATTCGAGCAATC |
| 39 | Sac4 | ACACACTGTGGAGTTTT |
| 40 | Sac4-2 | AAAACCGTTTCAATACA |
| 41 | Sac5 | GCAACTTTTCTTTGGG |
| 42 | Sac6 | TCATTAAATTTTGTCAA |
| 43 | Sac6-2 | GTCAAAACAAGAATTTT |

TABLE 1-2

| SEQ ID NO. | NAME OF OLIGO | SEQUENCE |
|---|---|---|
| 44 | Pano1 | ACACACATTGTCTAGTT |
| 45 | Pano3 | TATTGACTTAGCAAGAG |
| 46 | Pano4 | CTAATAAGCAGTCTTTC |
| 47 | Pano4-2 | CAGTCTTTCTGAAATAATG |
| 48 | Pano4-3 | CTAATAAGCAGTCTTTCT |
| 49 | Pano5 | GTTAAAACCTTTAACCA |
| 50 | Pano6 | TAGGCAGGTTTAGAAGT |
| 51 | Pano6-2 | ATATCAGCTAGGCAGG |
| 52 | Pano7 | GGCTCGGCTTAACAACA |
| 53 | HuvHgu1 | AGATCTTTTACAATAATGTGTA |
| 54 | HuvHgu2 | CGAAAGGTTCAAGGCAAA |
| 55 | HuvHgu3 | CGTTTTACTTTACAAGG |
| 56 | HuvHgu5 | AGGCAAAGGGTTGCTTT |
| 57 | CvaPme1 | CCAACACCACACTGTGTG |
| 58 | CvaPme2 | CACACGTCAACAAAAGA |
| 59 | CvaPme2-2 | GTCAACAAAAGATCTAAAAG |
| 60 | CvaPme3 | TGCGCAGAGCTGGCCG |
| 61 | CvaPme4 | AAACGTTGCGGACGAAG |
| 62 | CvaPme4-2 | ACGTTGCGGACGAAG |
| 63 | CvaPme4-3 | GCCGAAAAGAAACGTTG |
| 64 | CvaPme5 | TACATCGGGACGCTTTG |

TABLE 1-3

| SEQ ID NO. | NAME OF OLIGO | SEQUENCE | REMARKS |
|---|---|---|---|
| 65 | Nega-con | cctaatcggcttagcgtagg | Negative control capture to the control probe |

TABLE 1-3-continued

| SEQ ID NO. | NAME OF OLIGO | SEQUENCE | REMARKS |
|---|---|---|---|
| 66 | ITS18S16 | TTGATTACGTCCCTGCCCTTTG | Primer |
| 67 | ITS46 | GATATGCTTAAGTTCAGCGG | Primer |
| 68 | Posi-con template | ttgattacgtccctgcccttg gacgaacgctggccctacctaa tcgcgatagcgtaggagccacg gctaactacgtgcccgctgaac ttaagcatatc | Control probe |
| 69 | Posi-con | cctaatcgcgatagcgtagg | Positive control capture to the control probe |

The present invention also provides a method for detecting and/or identifying a microorganism in a test sample. The method comprises preparing a nucleic acid of the microorganism that is in the test sample, preparing a labeled probe using the nucleic acid as a template, performing hybridization of an oligonucleotide immobilized to a surface of a support with the labeled probe using the oligonucleotide array or the instrument for detecting the microorganism according to the present invention, and detecting signals derived from the hybridization.

A preferred test sample for the method to detect a microorganism according to the present invention is food, and among others malt alcoholic beverages are most preferred.

The present invention also provides a kit for detecting a microorganism. The kit is typically used for operating the method for detecting a microorganism according to the present invention. The kit comprises the instrument for detecting the microorganism according to the present invention. It is also preferred that the kit comprises reagents for use in the steps of hybridization, signal detection, probe preparation, and nucleic acid sequence preparation.

Hereinafter, embodiments of the present invention are more specifically described. It should be noted that the present invention is not limited to these embodiments.

[1] An oligonucleotide Array or an Instrument for Detecting a Microorganism According to the Present Invention In the oligonucleotide array or the instrument for detecting and/or identifying a microorganism in a test sample according to the present invention, an oligonucleotide that is based on a nucleotide sequence specific to the species or the genus to which the microorganism of interest belongs is immobilized to a surface of a support, such as a substrate, so that the microorganism in the test sample is detected and/or identified by hybridization of the oligonucleotide with a nucleic acid sequence derived from the test sample.

Unless otherwise specified, the term "a" or "an" used herein shall mean "one or more".

[Support]

The support for use in the instrument for detecting a microorganism according to the present invention can be any support that can provide stable immobilization with the oligonucleotide. Non-limiting examples of such support include a substrate made from synthetic resins, such as polycarbonate or plastic, glass and the like. A shape of the substrate is not particularly limited. For example, a board-like or a film-like substrate and the like can be suitably used.

Further, the oligonucleotides can be bound to the support using any methods well known to those skilled in the art (for example, see procedures described in Japanese National Phase PCT Laid-open Patent Publication Nos. 2003-530861; 2004-526402, etc.). For the oligonucleotide array or the instrument for detecting a microorganism according to the present invention, it is preferred that the support has carbodiimide groups or isocyanate groups attached on its surface, and a covalent bond is formed as a result of a reaction between the carbodiimide group or the isocyanate group and the oligonucleotide or a linker attached to the terminus of the oligonucleotide.

[Oligonucleotide Immobilized to a Surface of a Support]

The oligonucleotide immobilized to the surface of the support used in the oligonucleotide array or the instrument for detecting a microorganism can be any oligonucleotide that is based on a nucleotide sequence specific to the species or the genus to which the microorganisms of interest belong. A microorganism contained in a test sample that belongs to the species or the genus of interest can be detected by utilizing hybridization of the oligonucleotide with the nucleic acid derived from the test sample. It should be noted that the oligonucleotide prepared based on a nucleotide sequence specific to the species or the genus to which the subject microorganism belongs is hereinafter called "capture oligo" where appropriate.

The specific nucleotide sequence can be obtained by selecting a nucleotide sequence specific to the genus or the species from genomic nucleotide sequences of a subject microorganism. It is however preferred that the specific nucleotide sequence is obtained from the nucleotide sequence corresponding to the ribosomal RNA gene of the subject microorganism. Among others, the nucleotide sequence specific to the genus or the species is preferably obtained from DNA sequences corresponding to the spacer region (ITS region) located between the 18S ribosomal RNA gene and the 25S ribosomal RNA gene of the microorganism, since the ITS region is known to contain many of nucleotide sequences that are genus specific or species specific. The nucleotide sequence of the ITS region is available from database such as GenBank, EMBL, DDBL and the like.

A capture oligo can be designed based on the genus- or species-specific nucleotide sequence. Therefore, the capture oligo may be the genus- or the species-specific nucleotide sequence per se. Alternatively, the capture oligo may contain variations such as several nucleotides replacements, deletions, insertions and/or additions and the like. The positions for the variations are not particularly limited.

The length (the number of nucleotides) of the capture oligo is not particularly limited. However, detection of hybridization becomes difficult when it is too short. When it is too long, non-specific hybridization may result. After a series of analyses on optimum length of the capture oligo, the inventors determined that the optimum length was typically 12 to 24 base long, or more preferably 13 to 22 base long. However, the length of capture oligo is not limited to these. For example, the length of the capture oligo can be shorter by several bases (e.g., 8, 9, 10, 11 bases), or longer by several bases (e.g., 25 bases, 26 bases, 27 bases, 28 bases) than the above-specified range. The inventors have confirmed that the nucleotide length is largely dependent on the sequence profile (the content of a specific nucleotide, the number of repeats of a specific nucleotide), and that even a short chain allows for specific hybridization if it possesses a good bonding capacity.

In the case where the capture oligo has a steric structure such as a hairpin structure, loop structure or other structure that hinders hybridization of the capture oligo with the nucleic acids from a test sample, the steric structure can be removed by replacing one or more nucleotides that constitute the capture oligo with inosine or a nucleic acid that does not pair with any nucleotide.

A synthesis method of a capture oligo is not particularly limited. For example, a method described in Maniatis, T. et al., Molecular Cloning A Laboratory Manual, Second Edition, Cold Spring Harbor Laboratory Press (1989) may be used. Generally, the capture oligo can be synthesized using a commercially available DNA synthesizer.

In the oligonucleotide array or the instrument for detecting a microorganism according to the present invention, it is preferable that so-called control capture oligo as well as the oligonucleotide based on the nucleotide sequence specific to the species or the genus to which the subject microorganism belongs are immobilized on the surface of the support. The control capture oligo includes a positive control capture oligo and a negative control capture oligo (see Table 1-3). The positive control capture oligo is used to check whether the amplification reaction is operated well in a probe-preparing step as described below, and whether hybridization is operated well. The negative control capture oligo is used to check for non-specific hybridization, i.e., a false-positive hybridization signal. Therefore, the present invention also encompasses an array or an instrument for detecting a microorganism in which the positive control capture oligo and negative control capture oligo are immobilized on the surface of the support.

The positive control capture oligo may be any oligonucleotide that is designed based on a nucleotide sequence contained in the probe prepared from the subject microorganism. In the case where different subject microorganisms are detected using a single microorganism detecting instrument, a different positive control capture oligo may be designed for each of the subject microorganisms, or a single positive control capture oligo may be designed based on a common nucleotide sequence shared by the probes prepared from the different subject microorganisms. In the case where the probes prepared from different subject microorganisms do not share a common nucleotide sequence, a different positive control capture oligo may be designed for each of smaller groups of the subject microorganisms. Alternatively, a synthetic sequence may be designed so that it has a different sequence from a sequence of a subject microorganism but has a common primer sequence, and a part of the synthetic sequence may be used as a positive control capture oligo. Using such an artificial sequence as a template, a probe can be prepared (such a probe is herein called "control probe"), and the resulting probe is added to a probe prepared from a test sample. In this way, specificity of the hybridization can be tested. More details on the probes will be discussed below.

It is preferable that the negative control capture oligo be designed such that it has a nucleotide sequence of a positive control capture oligo with artificial substitution of one or more nucleotides but less than 20% of the total nucleotides of the sequence. The number of substituted nucleotides is determined taking into consideration of the hybridization conditions so that the negative control capture oligo does not hybridize with the probes derived from a subject microorganism.

The subject microorganism is not particularly limited, and is suitably selected from those contained in a test sample. For example, a microorganism that is likely to contaminate and spoil foods may be selected as a subject microorganism. Contamination of food by harmful microorganisms is a big concern for public health. In malt alcoholic beverages as represented by beer and low-malt beer, contamination by harmful microorganisms deteriorates product quality by causing turbidity, loss of flavor, or other undesirable effects. Therefore, there is a strong demand for a method that allows for quick and accurate detection and identification of those harmful microorganisms.

Examples of microorganisms, especially *Eumycetes*, which contaminates food including malt alcoholic beverages, include those belonging to genus of *Brettanomyces* (*Dekkera*), *Candida*, *Pichia*, *Hanseniaspora*, *Saccharomyces* except for those of brewer's yeast. Further, examples of *Eumycetes* that belong to genus of *Brettanomyces* (*Dekkera*) include *Brettanomyces* (*Dekkera*) *bruxellensis* and *Brettanomyces* (*Dekkera*) *anomala*. Further, examples of *Eumycetes* that belong to genus of *Saccharomyces* except for those of brewer's yeast include *Saccharomyces cerevisiae*, *Saccharomyces diastaticus* or *Saccharomyces bayanus*.

Further examples of *Eumycetes* that contaminate food, other than those listed above, include *Pichia anomala*, *Hanseniaspora uvarum*, *Hanseniaspora guilliermondii*, *Candida valida*, and *Pichia membranaefaciens*. However, subject microorganisms are not limited to those listed above.

The capture oligos for detecting and/or identifying the above-exemplified microorganisms include those oligonucleotides prepared based on a species specific sequence and derived from *Brettanomyces* (*Dekkera*) *bruxellensis*, *Brettanomyces* (*Dekkera*) *anomala*, *Saccharomyces cerevisiae*, *Saccharomyces diastaticus*, *Saccharomyces pastorianus*, *Saccharomyces bayanus*, *Pichia anomala*, *Hanseniaspora uvarum*, *Hanseniaspora guilliermondii*, *Candida valida*, and *Pichia membranaefaciens*. Specific examples of these oligonucleotides include, but are not limited to, any of the nucleotide sequences as represented by SEQ ID NOs.: 1-64.

The capture oligos that are immobilized to the surface of the support of the instrument for detecting a microorganism according to the present invention are not particularly limited, and can be any oligonucleotides that can hybridize with the probes prepared from the subject microorganisms. Therefore, the oligonucleotide of the present invention may consist only of a nucleotide sequence represented by any of SEQ ID NOs.: 1-64, or it may contain a nucleotide sequence other than the nucleotide sequence of any of SEQ ID NOs.: 1-64. The capture oligo that contains a sequence other than the sequence as represented by any of SEQ ID NOs.: 1-64 includes an oligonucleotide that has any of the sequences of SEQ ID NOs.: 1-64 with an extended nucleotide sequence at the 5'- or the 3'-terminal, or at both of the terminals of the oligonucleotide, wherein the extended sequence has been made based on the nucleotide sequence from each of the ITS regions. An instrument for detecting a microorganism in which such oligonucleotides are immobilized to a surface of a support is also included in the present invention.

At least one capture oligo may be immobilized on a support and there is no upper limit for the number of the capture oligo. Considering easy operability and speedy detection, it is preferable to detect microorganisms, which are detectable in a test sample, exhaustively on a single substrate when microorganisms contaminating a sample are to be detected. Therefore, it is most preferable that the instrument for detecting a microorganism according to the present invention is also constituted as so called a microarray-type instrument in which a multiple capture oligos that correspond to the species or the genus of the microorganisms of interest are immobilized on a single support. For example, when malt alcoholic beverages are the test sample, it is preferable to immobilize capture oligos that correspond to microorganisms belonging to *Brettanomyces*, *Saccharomyces diastaticus* and the like to the surface of the support.

[Immobilization of Oligonucleotides (Capture Oligs)]

The method to immobilize oligonucleotides to a surface of a support (e.g., a substrate) is not limited to any particular method, and any method known to those skilled in the art can be used as appropriate. For example, a common procedure used in hybridization methods such as physical adsorption, electrostatic bonding, molecular covalent bonding and the like. For the instrument for detecting a microorganism according to the present invention, it is preferable to use a substrate having attached a carbodimide group or an isocyanate group on the surface (U.S. Pat. No. 5,908,746; Japanese Laid-open Patent Publication No. 8-23975) for the immobilization. The oligonucleotides may be spotted on the support in an array or a matrix.

If the amount of the oligonucleotide spotted on the support is too small, any detection may be difficult because there may not be enough reaction between the oligonucleotides and the probes. In addition to such a technical problem, the high integration spotting is expensive and requires an expensive high-precision detection instrument, such as a scanner, for detection utilizing fluorescent labeling of the probes or chemiluminescence. Therefore, it is preferable to immobilize the oligonucleotides within a size of 10 to 1,000 μm diameter on the surface of the substrate. The method for spotting the oligonucleotides on the surface of the substrate is not limited to any particular method. For example, spotting can be performed by spotting a solution of the oligonucleotide on the substrate using a spotting machine. In this way, the oligonucleotide solution can be generally spotted in a generally round shape. Further reference can be made to, for example, Japanese Laid-open Patent Publication No. 2002-65274 (see, for example, description in paragraphs 0062 to 0066), for a method of immobilization of capture oligos to a support.

[2] The Method for Detecting of a Microorganism According to the Present Invention The method for detecting a microorganism according to the present invention is a method for detecting and/or identifying a microorganism in a test sample that comprises the steps of: preparing a nucleic acid of the microorganism that is present in the test sample; preparing a labeled probe using the nucleic acid as a template; hybridizing the labeled probe with an oligonucleotide prepared based on a sequence specific to the species or the genus to which the subject microorganism belongs; and detecting a signal from the hybridization. In the hybridization step of the present detection method, at least one oligonucleotide consisting of (or comprising) any of the nucleic acid sequences of SEQ ID NOs. 1-64, an oligonucleotide array for detecting a microorganism, an instrument for detecting a microorganism according to the present invention may be used. Using the oligonucleotide, the oligonucleotide array or the instrument according to the present invention, an exhaustive detection and/or identification of a microorganism can be made easily, quickly and accurately. In addition, food is a preferable test sample for use in the present detection method. Hereinafter, each step is specifically described.

[Nucleic Acid Preparation Step]

The nucleic acid preparation step is a step of preparation of nucleic acids of a microorganism contained in a test sample. Any of known nucleic acid preparation methods may be selected for use in preparation of nucleic acids from a test sample. For example, in the preparation of DNA, a DNA may be extracted using the method described in R-F. Wang, Molecular and Cellular Probes (2000) 14, 1-5. Other than such a typical preparation method, any of many alternative methods may be used as well. Further, a commercially available kit may also be used.

[Probe Preparation Step]

The probe preparation step is a step of preparation of a labeled probe using the nucleic acids prepared in the nucleic acid preparation step as a template. The probe can be prepared by nucleic acid amplification such that it comprises nucleotide sequences for a capture oligo and a positive control capture oligo. The method of the nucleic acid amplification includes, but not limited to, a DNA amplification method using PCR or a RNA amplification method using an in vitro transcription method.

For example, when the labeled probe is prepared by PCR, the primer used in the PCR is designed such that the probe comprises a nucleotide sequence complementary to both a capture oligo and a positive control capture oligo. It should be noted that the probe may be either longer or shorter than the capture oligo or the positive control capture oligo so long as it allows for the hybridization. The primer used in the PCR may be labeled beforehand to obtain a labeled probe. It is also possible to obtain a labeled probe by labeling the substrate of PCR (i.e., deoxynulceoside triphosphate). Alternatively, the probe may be labeled after the PCR. The labeling agents are not limited to particular ones, and labeling agents such as those used for probes generally used for hybridization such as fluorescent agents, haptens, radioactive agents and the like may be used. For example, the fluorescent agent includes fluorescein (FITC), rhodamine, phycoerythrin (PE), Texas red, cyanine series fluorescent dyes and the like, and the hapten includes biotin, digoxigenin (Dig), dinitrophenyl (DNP), fluorescein and the like.

[Hybridization Step]

The hybridization step is a step of hybridizing the probe with an oligonucleotide prepared based on a sequence specific to the species or the genus to which the microorganism of interest belongs [e.g., at least one oligonucleotide consisting of (or comprising) any of the nucleic acid sequences of SEQ ID NOs.: 1-64]. The hybridization may be performed on a membrane and the like to which the above oligonucleotides are immobilized. Alternatively, the oligonucleotide array or the instrument for detecting a microorganism according to the present invention may be used. Using the oligonucleotide array or the instrument for detecting a microorganism, an exhaustive detection and/or identification can be made easily, quickly and accurately. The method to perform the hybridization is not limited to a particular method, and any known method for nucleic acid hybridization may be selected and used as appropriate for the hybridization. A specific example of hybridization is described below.

The labeled probes are added to a hybridizing solution containing a saline solution such as standard saline citrate (SSC), a blocking solution such as bovine serum albumin (BSA), sodium dodecyl sulfate (SDS) and an additive to facilitate hybridization. When the probes are double stranded, they are denatured by applying heat, for example. Then, several micro liters of the labeled probe solution is dropped on a substrate, and the whole is heated for several hours (generally at 37° C. to 50° C.), so as to allow the labeled probes to hybridize with the oligonucleotides immobilized on the substrate. Thereafter, 5×SSC or 3M tetramethyl ammonium chloride is added onto the substrate, and the substrate is heated (generally at 37° C. to 50° C.) to remove labeled probes that did not form specific hybrids. As a result, only the specific hybrids selectively remain on the substrate.

It is preferable that the hybridization is performed under stringent conditions so that cross hybridization does not occur. The "stringent hybridization conditions" refer to conditions in which the probe hybridizes with the target partial sequence while there is substantially no hybridization occurs between the probe and a sequence other than the target sequence or a sequence that differs from the target sequence by an identifiable amount. The stringent hybridization conditions are sequence dependent, and also vary with ambient conditions. The longer the sequence, the higher the temperature at which specific hybridization occurs. Generally, the temperature for stringent conditions is selected such that it is 5° C. lower than the melting temperature ($T_m$) of the specific sequence under specified ionic strength and pH. $T_m$ is the temperature at which 50% of the probes complementary to the target sequence hybridize to the target sequence at equilibrium under predetermined ionic strength, pH and nucleic acid concentration. Generally, at $T_m$, 50% of the probes are occupied by the target because the target sequence is present in large excess. Typically, the stringent conditions are characterized by pH of 7.0-8.3, concentration of salt (such as Na and the like) being at least about 0.01 to 1.0 M, and a temperature of about 30° C. for a shorter probe (for example, 10-50 nucleotides). The stringent conditions can also be achieved by addition of destabilizing agents such as formamide.

As used herein, the phrase "specifically hybridize" or "capable of specifically hybridizing" means that a sequence can bind, be double stranded or hybridize substantially or only with a specific nucleotide sequence or a group of specific nucleotide sequences under stringent hybridization conditions when the sequence is present in a complex mixture of DNA or RNA. Generally, it is known that nucleic acids are denatured by elevated temperatures, or reduced concentrations of salts in a buffer containing the nucleic acids. Under low stringent conditions (such as low temperature and/or high salt concentrations), hybrid double strands (for example, DNA:DNA, RNA:RNA or RNA:DNA) are formed as a result of gradual cooling even if the paired sequence is not completely complementary. Therefore, the specificity of the hybridization is reduced under low stringent conditions. On the contrary, under high stringent conditions (for example, high temperature or low salt concentration), it is necessary to keep as little mismatch as possible for proper hybridization.

Those skilled in the art would understand that hybridization conditions can be selected such that an appropriate level of stringency is achieved. In one exemplary embodiment, hybridization is performed under low stringency conditions such as 6×SSPE-T at 37° C. (0.05% Triton X-100) to ascertain thorough hybridization. Thereafter, a wash is performed under high stringent conditions (such as 1×SSPE-T at 37° C.) to remove mismatch hybrid double strands. A serial wash can be performed with increasingly high stringency (for example, 0.25 SSPE-T at 37° C. to 50° C.) until a desired level of hybridization specificity. The stringency can be also increased by addition of agents such as formamide. The specificity of the hybridization can be verified by comparing the hybridization of the sequence with a variety of probable controls (for example, an expression level control, a standardization control, a mismatch control, etc.) with the hybridization of the sequence with a test probe.

Various methods for optimization of hybridization conditions are well known to those skilled in the art (for example, see P. Tijssen (Ed) "Laboratory Techniques in Biochemistry and Molecular Biology", vol. 24; Hybridization With Nucleic Acid Probes, 1993, Elsevier, N.Y.).

[Signal Detection Step]

In the signal detection step, the success or failure of hybridization in the hybridization step is determined. Generally, the signal detection step is carried out successively after the hybridization step.

A method used in the hybrid detecting step depends on the labeling material introduced into the probe prepared in the probe preparing step. That is, for the detection of hybrids, a fluorescent material, hapten, or other labeling materials introduced into the probe is used. As such, a method of detecting a labeling substance in the probe can be suitably selected from known methods.

For example, when using a hapten, a solution containing a conjugate (enzyme conjugate) of (i) a protein that recognizes the hapten or binds to the hapten and (ii) alkali phosphatase or horseradish peroxidase is applied onto the substrate. Then, the substrate is incubated for several ten minutes at room temperature. Note that, before allowing for the bonding reaction between the hapten and the enzyme conjugate, the regions of substrate other than those in which the oligonucleotides are immobilized may be completely coated with a protein such as casein. In this way, a non-specific absorption reaction between the enzyme conjugate and substrate can be avoided. This can be carried out by applying a solution of casein or other proteins onto the oligonucleotide-immobilized substrate, and by allowing the substrate to stand for several ten minutes at room temperature. After the completion of the bonding reaction between the enzyme conjugate and the hapten in the probe, the enzyme conjugate that did not bind to the hapten is washed away with a suitable buffer containing a surfactant. As a result, only the enzyme conjugate that formed a bond with the hapten in the probe remains on the substrate.

For the visualization of the hybrids, a compound is added that forms an insoluble compound only when there is a conjugate of the hapten and the enzyme conjugate. The insoluble compound turns visible by being amplified by a catalytic reaction. When alkali phosphatase is used for the enzyme conjugate, nitroblue tetrazolium chloride (NBT) and BCIP (5-bromo-4-chloro-3-indolyl phosphate, p-toluidine salt) are used as the added compounds. When the enzyme is horseradish peroxitase, TMB (3,3',5,5' tetramethyl benzidine) is used as the added compound, for example.

Determination of microorganism species contained in the test sample is made based on the hybridization signal such as pigmentation or fluorescence of the hybrids at the immobilized capture oligos. That is, if a hybridization signal is detected, it means that the test sample at the spot where the hybridization signal is seen contains a microorganism that corresponds to the oligonucleotides. It should be noted here that the presence of a hybridization signal at places where the positive control capture oligos are immobilized means that the test functions properly. The absence of a hybridization signal at the places where the negative control capture oligos are immobilized means that the hybridization was conducted under appropriate conditions.

[3] Microorganism Detecting Kit According to the Present Invention

A microorganism detecting kit according to the present invention is used to canny out the method for detecting a microorganism according to the present invention. As such, the microorganism detecting kit is not just limited to a particular form as long as it can be used to carry out the method for detecting a microorganism according to the present invention.

The microorganism detecting kit according to the present invention typically includes at least one oligonucleotide consisting of (or comprising) any of the nucleic acid sequences of SEQ ID NOs.: 1-64, an oligonucleotide array for detecting a microorganism, an instrument for detecting a microorganism according to the present invention. Using the kit comprising these, an exhaustive detection and/or identification can be made easily, quickly and accurately. It is also preferable that a microorganism detecting kit according to the present invention includes reagents used in the hybridization step and the signal detection step. Non-limiting examples of reagents used in the hybridization step include: a saline solution such as SSC (standard saline citrate); a blocking reagent such as bovine serum albumin (BSA), sodium dodecyl sulfate (SDS); and an additive for facilitating hybridization. Non-limiting examples of reagents used in the signal detection step include: a conjugate (enzyme conjugate) of a hapten-recognizing protein and an enzyme; and a chromogenic substrate such as NBT, BCIP, or TMB. The reagents are suitably selected depending on intended use, and included in the kit.

It is preferable that the microorganism detecting kit includes a reagent used in the probe preparing step, and more preferably a reagent used in the nucleic acid preparing step as well. Non-limiting examples of a reagent used in the probe preparing step include: a PCR buffer; a heat-resistant DNA polymerase; and a mixture containing deoxynucleoside triphosphate. Non-limiting examples of a reagent used in the nucleic acid preparing step include: a buffer for bacteriolysis; a DNA collecting column; and a DNA extracting buffer. The reagents are suitably selected depending on intended use, and included in the kit.

With the microorganism detecting kit according to the present invention (including the array or the instrument for detecting a microorganism and reagents used in the respective steps of the method), detection and/or identification of a microorganism contained in a test sample can be performed in about 6 hours from the receipt of the test sample.

[4] Use of the Present Invention

The oligonucleotide according to the present invention can be used as a probe for detecting and/or identifying a microorganism in a test sample. The subject microorganism includes those belonging to (1) *Brettanomyces* (*Dekkera*) *bruxellensis*, (2) *Brettanomyces* (*Dekkera*) *anomala*, (3) *Saccharomyces cerevisiae* or *Saccharomyces diastaticus*, *Saccharomyces pastorianus*, or *Saccharomyces bayanus*.

Further, the subject microorganism in the present invention includes (4) *Pichia anomala*, (5) *Hanseniaspora uvarum*, or (6) *Hanseniaspora guilliermondii*, *Candida valida* or *Pichia membranaefaciens*.

The oligonucleotide, the oligonucleotide array, the instrument, the method and the kit for detecting a microorganism can be used for any use, without limitation, as long as it requires determination of a microorganism. Specifically, during processes for manufacturing a variety of industrial products that are greatly affected by contamination with microorganisms, for example, the present invention can be suitably utilized in cases where there is a need to detect and/or identify microorganisms isolated from the industrial products or the environment of the production sites quickly and accurately.

Non-limiting representative examples of such industrial products from which subject microorganisms are obtained include foods, beverages, medical drugs, reagents, quasi-drugs, and disposable medical instruments. Among these industrial products, the present invention is particularly suitable for foods. Specifically, non-limiting examples of the foods include: bread, sweets of various kinds (including cold or frozen sweets), prepared food, dairy products, cereals, tofu, fried tofu, noodles, box lunch, seasonings, agricultural products such as wheat flour or meat, nutraceutical foods (including various supplements), and preserved food (canned food, frozen food, retort-packed food, etc.).

Among these examples, the present invention is particularly suitable for beer, low-malt beer, liqueur, low-alcoholic beverages (for example, malt alcoholic beverages with the alcohol content of less than 1%; beer-taste beverages) and the like, but not limited thereto.

The present invention is not limited to any of the embodiments described above, and a variety of modifications are possible within the scope of what is described in the claims. Any embodiments obtainable from any suitable combination of technical means disclosed for each of different embodiments are also within the scope of the present invention.

While the invention is susceptible to various modifications and alternative forms, a specific embodiment thereof will be described below in more detail by way of Examples with reference to the attached drawings. It should be understood, however, that it is not intended to limit the invention to the particular forms disclosed, but on the contrary, the invention is to cover all modifications, equivalents, and alternatives falling within the scope of the invention as defined in the appended claims.

EXAMPLES

[Synthesis of Oligonucleotides]

According to ordinary method, an oligonucleotide synthesizer (the product of Perkin-elmer Applied biosystems) was used to synthesize oligonucleotides. After deprotection, the product was dried. The dried mass of the oligonucleotide was dissolved using 10 mM Tris-HCl (pH=7.5) and 1 mM EDTA buffer, so as to prepare 100 pmol/µL of oligonucleotide solution. All the oligonucleotides used in the Example were synthesized according to this procedure. The oligonucleotides had nucleotide sequences as represented by SEQ ID NOs: 1 through 69. The oligonucleotides of SEQ ID NOs: 1 through 64 are capture oligos, SEQ ID NO: 65 is the negative control capture oligo for subject microorganisms, SEQ ID NO: 66-67 is the primer, SEQ ID NOs: 68 is the control probe, and SEQ ID NO.: 69 is the positive control capture oligo for the control probe. For each capture oligo, an amino group was ligated to the 5' end using the synthesizer. For each primer, biotin was adapted to the 5' end.

[Spotting of Capture Oligonucleotides on a Substrate]

Ten µl of a microspotting solution (TeleChem International Inc.) was mixed with a 10 µl solution containing an oligonucleotide having an amino group at the 5' end. The mixture was then placed in each well of a microtiter plate (the product of Greiner Laboratory Inc.). Then, the slide glass CarboStation for processing carbodiimido resin (the product of Nisshinbo Industries, Inc.) was set on a predetermined position of a spotting machine, and the spotting machine was operated. After the spotting, a stream of hot water was applied onto the slide glass for several seconds, followed by irradiation of 600 mJ ultraviolet light. After exposed to the steam for several more seconds, the slide glass was placed on a hot plate to remove water. Then, the slide glass was immersed for 30 minutes at room temperature in a 3% BSA (bovine serum albumin)-containing mixture of 100 mM Tris-HCl (pH=7.5), 100 mM NaCl, and 0.1% Triton X-100 for blocking, followed by washing with a 10mM Tris-HCl (pH=7.5) and 1 mM EDTA buffer. The slide glass was then dried at room temperature and was kept in cool and dark in a dried state for later use. FIG. 1(A) shows positions of oligonucleotides immobilized on a substrate of the microorganisms detecting instrument actually used in the Examples.

[Nucleic Acid Preparing Step]

For the specimens, 11 different species of microorganisms were used, including 2 species of *Brettanomyces*, 4 species of Saccharomyces, 2 species of Candida, 2 species of Pichia, and 2 species of Hanseniaspora. Table 2 represents microorganisms used as specimens.

TABLE 2

Brettanomyces(Dekkera) bruxellensis
Brettanomyces(Dekkera) anomala
Saccharomyces cerevisiae
Saccharomyces diastaticus
Saccharomyces pastorianus
Saccharomyces bayanus
Pichia anomala
Hanseniaspora uvarum
Hanseniaspora guilliermondii
Candida valida
Pichia menbranaefaciens From cells of each species cultured under optimum culture conditions, genomic DNA of each microorganisms was prepared using the Genomic DNA Purification Kit (the product of EdgeBioSystems, Cat. No. #85171).

[Probe Preparing Step]

Using the DNA of each microorganism species as a template, a probe nucleic acid was prepared by PCR. The reaction mixture of PCR contained 1 unit of Taq polymerase; 10 pmol each of biotinylated primers (SEQ ID NOs: 66 and 67); 5 µl of a reaction buffer (10×); 10 nmol each of dNTP; and 100 ng of template DNA. The reaction mixture had a total volume of 50 µl with the addition of sterilized distilled water. The mixture was maintained for 3 minutes at 95° C. with a thermal cycler, and the reaction was carried out in 30 cycles at 95° C. for 30 seconds, at 55° C. for 15 seconds, and at 72° C. for 1 minute. The mixture was then maintained at 72° C. for 5 minutes before finishing the reaction.

Meanwhile, a synthetic sequence (control probe) was prepared that differed from the sequence of the subject microorganism except for the primer sequence. Using the control probe as a template, PCR was carried out to prepare a biotinylated control probe. The reaction mixture of PCR had the same composition as above except that 1 ng of template DNA was used. The reaction temperatures and the number of the cycles for the reactions were also the same as above. The reaction mixture was directly used as a probe solution in the later hybridization step, without purifying the probe.

[Hybridization Step and Signal Detecting Step]

Three µl of the probe nucleic acid solution was mixed with 1 µl of a biotinylation control probe solution and 16 µl of an ArrayIT Unihyb Hybridization Solution (the product of TeleChem International Inc.). The mixture was heated for 1 minute at 100° C., and placed in ice for 5 minutes. A total amount of the probe nucleic acid solution was then placed on the capture oligo-immobilized substrate, and a cover glass was placed thereon. Then, the substrate was placed in a moisturizing container, and allowed to stand for 120 minutes in an incubator maintained at 37° C. Out of the incubator, the substrate was immediately immersed in a 2×SSC solution (2×SSC:0.033 M NaCl, 0.033 M sodium citrate) at room temperature, the cover glass was removed, and the substrate was immersed in the 2×SSC solution for 5 minutes at a maintained temperature of 37° C.

The substrate was taken out of the 2×SSC solution, set in a centrifuge (the product of Beckman), and centrifuged for 1 minute at 2,000 rpm. Thereafter, 1.4 mL of avidin-biotinylation peroxidase conjugate prepared by using the VECTASTAIN Elite ABC kit (VECTOR) was dropped on the substrate, and the substrate was allowed to stand for 30 minutes at room temperature, followed by washing in PBS (10 mM sodium phosphate (pH=7.5), and 0.9% sodium chloride).

Thereafter, 1.4 mL of chromogenic solution prepared by using the TMB substrate kit for peroxidase (VECTOR) was dropped on the substrate, and the substrate was allowed to stand for 30 minutes at room temperature. The substrate was then washed with distilled water to stop the chromogenic reaction.

[Determination]

The hybridized region was scanned at 600 dpi using the EPSON scanner GT-8700F with its transmission unit. The presence or absence of a signal was confirmed by visual inspection of the scanned image. As an example, FIG. 1(B) depicts a scanned image for Dekkera bruxellensis. FIG. 1(A) shows positions of oligonucleotides on the substrate.

[Results]

Tables 3 through 13 represent results for the 11 species of microorganisms used as specimens. In the tables, "o" denotes spots that produced signals, and "-" denotes spots that did not produce any signals. As is clear from Tables 3 to 13, in all cases, for the control probe, the positive control capture oligo (SEQ ID NO: 69) exhibited a signal, while no signal was observed in the negative control capture oligo. It was therefore confirmed that the amplification and hybridization both functioned properly. From this, it was confirmed that the nucleic acids prepared from the microorganisms were amplified. Note that, the discussions below disregard development of a signal in the positive control capture oligo (SEQ ID NO: 69).

Table 3 shows the result for Brettanomyces (Dekkera) bruxellensis. For Brettanomyces (Dekkera) bruxellensis, signals were observed only at 16 locations of the capture oligos for detecting Brettanomyces (Dekkera) bruxellensis (SEQ ID NOs: 1-14 and 23, 24) (see FIG. 1). Similarly, Table 4 shows the result for Brettanomyces (Dekkera) anomala. For Brettanomyces (Dekkera) anomala, signals were observed only at 17 locations of the capture oligos for detecting Brettanomyces (Dekkera) anomala (SEQ ID NOs: 7, 9 and 15-29). Table 5 shows the result for Saccharomyces cerevisiae. For Saccharomyces cerevisiae, signals were observed only at 14 locations of the capture oligos for detecting Saccharomyces (SEQ ID NOs: 30 to 43). Table 6 shows the results for Saccharomyces diastaticus. For Saccharomyces diastaticus, signals were observed only at 14 locations of the capture oligos for detecting Saccharomyces (SEQ ID NOs.: 30-43). Table 7 shows the result for Saccharomyces pastorianus. For Saccharomyces pastorianus, a signal was observed at at least 5 locations out of the 14 locations of the capture oligos for detecting Saccharomyces (SEQ ID NOs.: 30-43). Table 8 shows the result for Saccharomyces bayanus. For Saccharomyces bayanus, signals were observed at at least 5 locations out of the 14 locations of the capture oligos for detecting Saccharomyces (SEQ ID NOs.: 30-43). Table 9 shows the result for Pichia anomala. For Pichia anomala, signals were observed only at 9 locations of the capture oligos for detecting Pichia anomala (SEQ ID NOs.: 44-52). Table 10 shows the result for Hanseniaspora uvarum. For Hanseniaspora uvarum, signals were observed only at 4 locations of the capture oligos for detecting Hanseniaspora uvarum and Hanseniaspora guilliermondii (SEQ ID NOs.: 53-56). Table 11 shows the result for Hanseniaspora guilliermondii. For Hanseniaspora guilliermondii, signals were observed only at the 4 locations of the capture oligos for detecting Hanseniaspora uvarum and Hanseniaspora guilliermondii (SEQ ID NOs.: 53-56). Table 12 shows the result for Candida Valida. For Candida valida, signals were observed only at the 8 locations of the capture oligos for Candida valida and Pichia membranaefaciens is (SEQ ID NOs.: 57-64). Table 13 shows the result for Pichia membranaefaciens. For Pichia

*membranaefaciens*, a signal was observed only at the 8 locations of the capture oligos for Candida valida and *Pichia membranaefaciens* (SEQ ID NOs.: 57-64).

TABLE 3

Subject microorganism: *Brettanomyces(Dekkera) bruxellensis*

| Names of tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 o | 2 o | | |
| | 3 o | | | |
| | 4 o | 5 o | 6 o | |
| | 7 o | 8 o | 9 o | |
| | 10 o | 11 o | 12 o | |
| | 13 o | 14 o | | |
| *Brettanomyces(Dekkera) anomala* | 15 — | 16 — | | |
| | 17 — | 18 — | | |
| | 19 — | 20 — | | |
| | 21 — | 22 — | | |
| | 23 o | 24 o | 25 — | 26 — |
| | 27 — | 28 — | 29 — | |
| *Saccharomyces cerevisiae,* | 30 — | 31 — | | |
| *Saccharomyces diastaticus,* | 32 — | 33 — | | |
| *Saccharomyces pastorianus,* | 34 — | 35 — | 36 — | 37 — 38 — |
| *Saccharomyces bayanus* | 39 — | 40 — | | |
| | 41 — | | | |
| | 42 — | 43 — | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum,* | 53 — | | | |
| *Hanseniaspora guilliermondii* | 54 — | | | |
| | 55 — | | | |
| | 56 — | | | |
| *Candida valida,* | 57 — | | | |
| *Pichia menbranaefaciens* | 58 — | 59 — | | |
| | 60 — | | | |
| | 61 — | 62 — | 63 — | |
| | 64 — | | | |

TABLE 4

Subject microorganism: *Brettanomyces(Dekkera) anomala*

| Names of tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 o | 8 — | 9 o | |
| | 10 — | 11 — | 12 — | |
| | 13 — | 14 — | | |
| *Brettanomyces(Dekkera) anomala* | 15 o | 16 o | | |
| | 17 o | 18 o | | |
| | 19 o | 20 o | | |
| | 21 o | 22 o | | |
| | 23 o | 24 o | 25 o | 26 o |
| | 27 o | 28 o | 29 o | |
| *Saccharomyces cerevisiae,* | 30 — | 31 — | | |
| *Saccharomyces diastaticus,* | 32 — | 33 — | | |
| *Saccharomyces pastorianus,* | 34 — | 35 — | 36 — | 37 — 38 — |
| *Saccharomyces bayanus* | 39 — | 40 — | | |
| | 41 — | | | |
| | 42 — | 43 — | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |

TABLE 4-continued

Subject microorganism: *Brettanomyces(Dekkera) anomala*

| Names of tested microorganisms | SEQ ID NO.:/ "o" = with signal, "—" = w/o signal detected | | |
|---|---|---|---|
| *Hanseniaspora uvarum,* | 53 — | | |
| *Hanseniaspora guilliermondii* | 54 — | | |
| | 55 — | | |
| | 56 — | | |
| *Candida valida,* | 57 — | | |
| *Pichia menbranaefaciens* | 58 — | 59 — | |
| | 60 — | | |
| | 61 — | 62 — | 63 — |
| | 64 — | | |

TABLE 5

Subject microorganism: *Saccharomyces cerevisiae*

| Names of tested microorganisms | SEQ ID NO.:/ "o" = with signal, "—" = w/o signal detected | | | | |
|---|---|---|---|---|---|
| Positive control | 69 o | | | | |
| Negative control | 65 — | | | | |
| *Brettanomyces(Dekkera) bruxellensis* | 1 — | 2 — | | | |
| | 3 — | | | | |
| | 4 — | 5 — | 6 — | | |
| | 7 — | 8 — | 9 — | | |
| | 10 — | 11 — | 12 — | | |
| | 13 — | 14 — | | | |
| *Brettanomyces(Dekkera) anomala* | 15 — | 16 — | | | |
| | 17 — | 18 — | | | |
| | 19 — | 20 — | | | |
| | 21 — | 22 — | | | |
| | 23 — | 24 — | 25 — | 26 — | |
| | 27 — | 28 — | 29 — | | |
| *Saccharomyces cerevisiae,* | 30 o | 31 o | | | |
| *Saccharomyces diastaticus,* | 32 o | 33 o | | | |
| *Saccharomyces pastorianus,* | 34 o | 35 o | 36 o | 37 o | 38 o |
| *Saccharomyces bayanus* | 39 o | 40 o | | | |
| | 41 o | | | | |
| | 42 o | 43 o | | | |
| *Pichia anomala* | 44 — | | | | |
| | 45 — | | | | |
| | 46 — | 47 — | 48 — | | |
| | 49 — | | | | |
| | 50 — | 51 — | | | |
| | 52 — | | | | |
| *Hanseniaspora uvarum,* | 53 — | | | | |
| *Hanseniaspora guilliermondii* | 54 — | | | | |
| | 55 — | | | | |
| | 56 — | | | | |
| *Candida valida,* | 57 — | | | | |
| *Pichia menbranaefaciens* | 58 — | 59 — | | | |
| | 60 — | | | | |
| | 61 — | 62 — | 63 — | | |
| | 64 — | | | | |

TABLE 6

Subject microorganism: *Saccharomyces diastaticus*

| Names of tested microorganisms | SEQ ID NO.:/ "o" = with signal, "—" = w/o signal detected | | |
|---|---|---|---|
| Positive control | 69 o | | |
| Negative control | 65 — | | |
| *Brettanomyces(Dekkera) bruxellensis* | 1 — | 2 — | |
| | 3 — | | |
| | 4 — | 5 — | 6 — |
| | 7 — | 8 — | 9 — |
| | 10 — | 11 — | 12 — |
| | 13 — | 14 — | |

TABLE 6-continued

Subject microorganism: *Saccharomyces diastaticus*

| Names of tested microorganisms | SEQ ID NO.:/ "o" = with signal, "—" = w/o signal detected | | | |
|---|---|---|---|---|
| *Brettanomyces((Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae,* | 30 o | 31 o | | |
| *Saccharomyces diastaticus,* | 32 o | 33 o | | |
| *Saccharomyces pastorianus,* | 34 o | 35 o | 36 o | 37 o  38 o |
| *Saccharomyces bayanus* | 39 o | 40 o | | |
| | 41 o | | | |
| | 42 o | 43 o | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum,* | 53 — | | | |
| *Hanseniaspora guilliermondii* | 54 — | | | |
| | 55 — | | | |
| | 56 — | | | |
| *Candida valida,* | 57 — | | | |
| *Pichia menbranaefaciens* | 58 — | 59 — | | |
| | 60 — | | | |
| | 61 — | 62 — | 63 — | |
| | 64 — | | | |

TABLE 7

Subject microorganism: *Saccharomyces pastorianus*

| Names of tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 — | 8 — | 9 — | |
| | 10 — | 11 — | 12 — | |
| | 13 — | 14 — | | |
| *Brettanomyces(Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae,* | 30 — | 31 — | | |
| *Saccharomyces diastaticus,* | 32 — | 33 — | | |
| *Saccharomyces pastorianus,* | 34 — | 35 — | 36 — | 37 —  38 — |
| *Saccharomyces bayanus* | 39 o | 40 o | | |
| | 41 o | | | |
| | 42 o | 43 o | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum,* | 53 — | | | |
| *Hanseniaspora guilliermondii* | 54 — | | | |
| | 55 — | | | |
| | 56 — | | | |
| *Candida valida,* | 57 — | | | |
| *Pichia menbranaefaciens* | 58 — | 59 — | | |
| | 60 — | | | |
| | 61 — | 62 — | 63 — | |
| | 64 — | | | |

TABLE 8

Subject microorganism: *Saccharomyces bayanus*

| Names or tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 — | 8 — | 9 — | |
| | 10 — | 11 — | 12 — | |
| | 13 — | 14 — | | |
| *Brettanomyces(Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae,* | 30 — | 31 — | | |
| *Saccharomyces diastaticus,* | 32 — | 33 — | | |
| *Saccharomyces pastorianus,* | 34 — | 35 — | 36 — | 37 —  38 — |
| *Saccharomyces bayanus* | 39 o | 40 o | | |
| | 41 o | | | |
| | 42 o | 43 o | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum,* | 53 — | | | |
| *Hanseniaspora guilliermondii* | 54 — | | | |
| | 55 — | | | |
| | 56 — | | | |
| *Candida valida,* | 57 — | | | |
| *Pichia menbranaefaciens* | 58 — | 59 — | | |
| | 60 — | | | |
| | 61 — | 62 — | 63 — | |
| | 64 — | | | |

TABLE 9

Subject microorganism: *Pichia anomala*

| Names or tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 — | 8 — | 9 — | |
| | 10 — | 11 — | 12 — | |
| | 13 — | 14 — | | |
| *Brettanomyces(Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae,* | 30 — | 31 — | | |
| *Saccharomyces diastaticus,* | 32 — | 33 — | | |
| *Saccharomyces pastorianus,* | 34 — | 35 — | 36 — | 37 —  38 — |
| *Saccharomyces bayanus* | 39 — | 40 — | | |
| | 41 — | | | |
| | 42 — | 43 — | | |
| *Pichia anomala* | 44 o | | | |
| | 45 o | | | |
| | 46 o | 47 o | 48 o | |
| | 49 o | | | |
| | 50 o | 51 o | | |
| | 52 o | | | |

TABLE 9-continued

Subject microorganism: *Pichia anomala*

| Names or tested microorganisms | SEQ ID NO.:/ "o" = with signal, "—" = w/o signal detected | | | |
|---|---|---|---|---|
| *Hanseniaspora uvarum*, *Hanseniaspora guilliermondii* | 53 — | | | |
| | 54 — | | | |
| | 55 — | | | |
| | 56 — | | | |
| *Candida valida*, *Pichia menbranaefaciens* | 57 — | | | |
| | 58 — | 59 — | | |
| | 60 — | | | |
| | 61 — | 62 — | 63 — | |
| | 64 — | | | |

TABLE 10

Subject microorganism: *Hanseniaspora uvarum*

| Names or tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 — | 8 — | 9 — | |
| | 10 — | 11 — | 12 — | |
| | 13 — | 14 — | | |
| *Brettanomyces(Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae*, *Saccharomyces diastaticus*, *Saccharomyces pastorianus*, *Saccharomyces bayanus* | 30 — | 31 — | | |
| | 32 — | 33 — | | |
| | 34 — | 35 — | 36 — | 37 — 38 — |
| | 39 — | 40 — | | |
| | 41 — | | | |
| | 42 — | 43 — | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum*, *Hanseniaspora guilliermondii* | 53 o | | | |
| | 54 o | | | |
| | 55 o | | | |
| | 56 o | | | |
| *Candida valida*, *Pichia menbranaefaciens* | 57 — | | | |
| | 58 — | 59 — | | |
| | 60 — | | | |
| | 61 — | 62 — | 63 — | |
| | 64 — | | | |

TABLE 11

Subject microorganism: *Hanseniaspora guilliermondii*

| Names or tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 — | 8 — | 9 — | |
| | 10 — | 11 — | 12 — | |
| | 13 — | 14 — | | |

TABLE 11-continued

Subject microorganism: *Hanseniaspora guilliermondii*

| Names or tested microorganisms | SEQ ID NO.:/ "o" = with signal, "—" = w/o signal detected | | | |
|---|---|---|---|---|
| *Brettanomyces(Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae*, *Saccharomyces diastaticus*, *Saccharomyces pastorianus*, *Saccharomyces bayanus* | 30 — | 31 — | | |
| | 32 — | 33 — | | |
| | 34 — | 35 — | 36 — | 37 — 38 — |
| | 39 — | 40 — | | |
| | 41 — | | | |
| | 42 — | 43 — | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum*, *Hanseniaspora guilliermondii* | 53 o | | | |
| | 54 o | | | |
| | 55 o | | | |
| | 56 o | | | |
| *Candida valida*, *Pichia menbranaefaciens* | 57 — | | | |
| | 58 — | 59 — | | |
| | 60 — | | | |
| | 61 — | 62 — | 63 — | |
| | 64 — | | | |

TABLE 12

Subject microorganism: *Candida valida*

| Names or tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 — | 8 — | 9 — | |
| | 10 — | 11 — | 12 — | |
| | 13 — | 14 — | | |
| *Brettanomyces(Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae*, *Saccharomyces diastaticus*, *Saccharomyces pastorianus*, *Saccharomyces bayanus* | 30 — | 31 — | | |
| | 32 — | 33 — | | |
| | 34 — | 35 — | 36 — | 37 — 38 — |
| | 39 — | 40 — | | |
| | 41 — | | | |
| | 42 — | 43 — | | |
| Pichia anomala | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum*, *Hanseniaspora guilliermondii* | 53 — | | | |
| | 54 — | | | |
| | 55 — | | | |
| | 56 — | | | |
| *Candida valida*, *Pichia menbranaefaciens* | 57 o | | | |
| | 58 o | 59 o | | |
| | 60 o | | | |
| | 61 o | 62 o | 63 o | |
| | 64 o | | | |

TABLE 13

Subject microorganism: *Pichia menbranaefaciens*

| Names or tested microorganisms | SEQ ID NO.:/ "o" = with signal, "—" = w/o signal detected | | | |
|---|---|---|---|---|
| Positive control | 69 o | | | |
| Negative control | 65 — | | | |
| *Brettanomyces(Dekkera) bruxellensis* | 1 — | 2 — | | |
| | 3 — | | | |
| | 4 — | 5 — | 6 — | |
| | 7 — | 8 — | 9 — | |
| | 10 — | 11 — | 12 — | |
| | 13 — | 14 — | | |
| *Brettanomyces(Dekkera) anomala* | 15 — | 16 — | | |
| | 17 — | 18 — | | |
| | 19 — | 20 — | | |
| | 21 — | 22 — | | |
| | 23 — | 24 — | 25 — | 26 — |
| | 27 — | 28 — | 29 — | |
| *Saccharomyces cerevisiae,* | 30 — | 31 — | | |
| *Saccharomyces diastaticus,* | 32 — | 33 — | | |
| *Saccharomyces pastorianus,* | 34 — | 35 — | 36 — | 37 — 38 — |
| *Saccharomyces bayanus* | 39 — | 40 — | | |
| | 41 — | | | |
| | 42 — | 43 — | | |
| *Pichia anomala* | 44 — | | | |
| | 45 — | | | |
| | 46 — | 47 — | 48 — | |
| | 49 — | | | |
| | 50 — | 51 — | | |
| | 52 — | | | |
| *Hanseniaspora uvarum,* | 53 — | | | |
| *Hanseniaspora guilliermondii* | 54 — | | | |
| | 55 — | | | |
| | 56 — | | | |
| *Candida valida,* | 57 o | | | |
| *Pichia menbranaefaciens* | 58 o | 59 o | | |
| | 60 o | | | |
| | 61 o | 62 o | 63 o | |
| | 64 o | | | |

The above results show that, for each microorganism tested, chromogenic reaction was observed only at spots to which capture oligos that were specific to each microorganism were immobilized, and that no unspecific chromogenic reactions were observed. Therefore, it has been confirmed that it is possible to detect the microorganisms listed in Table 2 in a species specific manner using the microorganism detection instrument manufactured in the present Example

INDUSTRIAL APPLICABILITY

The present invention provides an instrument, a method and a kit for detecting a microorganism contaminating a subject test sample, which enables one to quickly and accurately identify the microorganism with an easy operation. Therefore, the present invention can be used for controls of hygiene, processes, and quality in industries such as food industries, beverage industries, pharmaceutical industries and the like.

The invention claimed is:

1. An oligonucleotide array for detecting the presence of a microorganism in a test sample, comprising any combination of the oligonucleotides of the following (A) and (B):
   (A) at least one oligonucleotide consisting of any one of the nucleic acid sequences selected from the group consisting of the nucleic acid sequences of SEQ ID NOs.: 1-6, 8, and 10-14, to detect *Brettanomyces (Dekkera) bruxellensis*; and
   (B) at least one oligonucleotide consisting of any one of the nucleic acid sequences selected from the group consisting of the nucleic acid sequences of SEQ ID NOs.: 15-22 and 25-29, to detect *Brettanomyces (Dekkera) anomala*, wherein said oligonucleotide is immobilized to a support.

2. The oligonucleotide array according to claim 1, wherein said test sample is food.

3. An instrument for detecting and/or identifying that a microorganism in a test sample belongs to any one or more of groups of a microorganism selected from the following groups of microorganisms (i) to (vii):
   (i) a microorganism belonging to *Brettanomyces (Dekkera) bruxellensis*;
   (ii) a microorganism belonging to *Brettanomyces (Dekkera) anomala*;
   (iii) a microorganism belonging to *Saccharomyces cerevisiae, Saccharomyces diastaticus, Saccharomyces pastorianus*, or *Saccharomyces bayanus*;
   (iv) a microorganism belonging to *Pichia anomala*;
   (v) a microorganism belonging to *Hanseniaspora uvarum* or *Hanseniaspora guilliermondii*;
   (vi) a microorganism belonging to *Candida valida* or *Pichia membranaefaciens*; and
   (vii) a microorganism belonging to *Brettanomyces (Dekkera) bruxellensis* or *Brettanomyces (Dekkera) anomala*,
   wherein said instrument comprises a support to which at least two oligonucleotides that specifically hybridize to the complementary strand of the nucleic acid of the microorganism that belongs to either of the selected plurality of the groups are immobilized, and wherein said instrument comprises an oligonucleotide consisting of one or more of the nucleic sequences of SEQ ID NOs: 1-6, 8, and 10-14, and an oligonucleotide consisting of one or more of the nucleic acid sequence selected from the group consisting of the nucleic acid sequences of SEQ ID NOs.: 15-22 and 25-29.

4. The instrument according to claim 3, which further comprises an oligonucleotide probe consisting of any of the nucleic acid sequences selected from the group consisting of the nucleic acid sequences of SEQ ID NOs.: 30-43.

5. The instrument according to claim 3, which further comprises an oligonucleotide probe consisting of any of the nucleic acid sequences selected from the group consisting of the nucleic acid sequences of SEQ ID NOs.: 44-52.

6. The instrument according to claim 3, which further comprises an oligonucleotide probe consisting of any of the nucleic acid sequences selected from the group consisting of the nucleic acid sequences of SEQ ID NOs.: 53-56.

7. The instrument according to claim 3, which further comprises an oligonucleotide probe consisting of any of the nucleic acid sequences selected from the group consisting of the nucleic acid sequences of SEQ ID NOs.: 57-64.

8. The instrument according to claim 3, which further comprises an oligonucleotide probe consisting of any of the nucleic acid sequences selected from the group consisting of the nucleic acid sequences of SEQ ID NOs.: 7, 9, 23, and 24.

9. The instrument according to claim 3, wherein said support has carbodiimide group or an isocyanate group on the surface, and wherein said oligonucleotide probe is immobilized to the support through a covalent bond formed between the carbodiimide group or the isocyanate group and the oligonucleotide probe or a linker attached to a terminal residue of the oligonucleotide probe as a result of reaction thereof.

10. A method for detecting a microorganism in a test sample, identifying a group to which a microorganism in a test sample belongs, or detecting a microorganism in a test sample and identifying a group to which said microorganism belongs, comprising:
    preparing a nucleic acid of a microorganism that is in a test sample;
    preparing a labeled probe using said nucleic acid as a template;
    hybridizing said labeled probe with an oligonucleotide probe immobilized to a surface of a support, using the oligonucleotide array according to claim 1, or the instrument according to claim 3; and
    detecting signals derived from said hybridization.

11. The method according to claim 10, wherein said test sample is food.

12. A kit for detecting a microorganism for performing the method according to claim 10, comprising a oligonucleotide array, wherein the oligonucleotide array comprises an oligonucleotide probe consisting of the nucleic acid sequence selected from the group consisting of the nucleic acid sequences of SEQ ID NOs.: 1-64, wherein said oligonucleotide probe is immobilized to a support, or a instrument for detecting and/or identifying that a microorganism in a test sample belongs to any one or more of groups of a microorganism selected from the following groups of microorganisms (i) to (vii):
    (i) a microorganism belonging to *Brettanomyces (Dekkera) bruxellensis*;
    (ii) a microorganism belonging to *Brettanomyces (Dekkera) anomala*;
    (iii) a microorganism belonging to *Saccharomyces cerevisiae, Saccharomyces diastaticus, Saccharomyces pastorianus*, or *Saccharomyces bayanus*;
    (iv) a microorganism belonging to *Pichia anomala*;
    (v) a microorganism belonging to *Hanseniaspora uvarum* or *Hanseniaspora guilliermondii*;
    (vi) a microorganism belonging to *Candida valida* or *Pichia membranaefaciens*; and (vii) a microorganism belonging to *Brettanomyces (Dekkera) bruxellensis* or *Brettanomyces (Dekkera) anomala*, wherein the instrument comprises a support to which at least one oligonucleotide probe that specifically hybridizes to a complementary strand of the nucleic acid of the microorganism that belongs to the selected group is immobilized, or at least two oligonucleotide probes that specifically hybridize to the complementary strand of the nucleic acid of the microorganism that belongs to either of the selected plurality of the groups are immobilized, wherein the oligonucleotide probe or probes consist of the nucleic acid sequence selected from the group consisting of the nucleic acid sequences of SEQ ID NOs.: 1-64.

13. The kit for according to claim 12 further comprising a reagent for use in the steps of said hybridization and said detection of the signals.

14. The kit according to claim 12 further comprising a reagent for use in the steps of the preparation of the probe and/or the preparation of a nucleic acid.

15. The array according to claim 1, which further comprises (C) at least one oligonucleotide consisting of any one of the nucleic acid sequences selected from the group consisting of the nucleic acid sequences of SEQ ID NOs.: 30-43, to detect *Saccharomyces cerevisiae, Saccharomyces diastaticus, Saccharomyces pastorianus,* or *Saccharomyces bayanu*, wherein said oligonucleotide is immobilized to the support.

16. The array according to claim 1, which further comprises (D) at least one oligonucleotide consisting of any one of the nucleic acid sequences selected from the group consisting of the nucleic acid sequences of SEQ ID NOs.: 44-52, to detect *Pichia anomala*, wherein said oligonucleotide is immobilized to the support.

17. The array according to claim 1, which further comprises (E) at least one oligonucleotide consisting of any one of the nucleic acid sequences selected from the group consisting of the nucleic acid sequences of SEQ ID NOs.: 53-56, to detect *Hanseniaspora uvarum* or *Hanseniaspora guilliermondii*, wherein said oligonucleotide is immobilized to the support.

18. The array according to claim 1, which further comprises (F) at least one oligonucleotide consisting of any one of the nucleic acid sequences selected from the group consisting of the nucleic acid sequences of SEQ ID NOs.: 57-64, to detect *Candida valida* or *Pichia membranaefaciens*, wherein said oligonucleotide is immobilized to the support.

19. The array according to claim 1, which further comprises (G) at least one oligonucleotide consisting of any one of the nucleic acid sequences selected from the group consisting of the nucleic acid sequences of SEQ ID NOs.: 7, 9, 23 and 24, to detect *Brettanomyces (Dekkera) bruxellensis* or *Brettanomyces (Dekkera) anomala*, wherein said oligonucleotide is immobilized to the support.

* * * * *

SEQUENCE LISTING

```
<160> NUMBER OF SEQ ID NOS: 69

<210> SEQ ID NO 1
<211> LENGTH: 22
<212> TYPE: DNA
<213> ORGANISM: Artificial
<220> FEATURE:
<223> OTHER INFORMATION: Probe

<400> SEQUENCE: 1
aaggataaaa atacattaaa tt                                                 22

<210> SEQ ID NO 2
<211> LENGTH: 20
<212> TYPE: DNA
<213> ORGANISM: Artificial
<220> FEATURE:
<223> OTHER INFORMATION: Probe

<400> SEQUENCE: 2
ggataaaaat acattaaatt                                                    20

<210> SEQ ID NO 3
<211> LENGTH: 17
<212> TYPE: DNA
<213> ORGANISM: Artificial
<220> FEATURE:
<223> OTHER INFORMATION: Probe

<400> SEQUENCE: 3
```

-continued

| | |
|---|---|
| gcagacacgt ggataag | 17 |

<210> SEQ ID NO 4
<211> LENGTH: 20
<212> TYPE: DNA
<213> ORGANISM: Artificial
<220> FEATURE:
<223> OTHER INFORMATION: Probe

<400> SEQUENCE: 4

| | |
|---|---|
| ggataatgat ttaaggtttc | 20 |

<210> SEQ ID NO 5
<211> LENGTH: 16
<212> TYPE: DNA
<213> ORGANISM: Artificial
<220> FEATURE:
<223> OTHER INFORMATION: Probe

<400> SEQUENCE: 5

| | |
|---|---|
| tgatttaagg tttcgg | 16 |

<210> SEQ ID NO 6
<211> LENGTH: 17
<212> TYPE: DNA
<213> ORGANISM: Artificial
<220> FEATURE:
<223> OTHER INFORMATION: Probe

<400> SEQUENCE: 6

| | |
|---|---|
| tgagggata atgattt | 17 |

<210> SEQ ID NO 7
<211> LENGTH: 17
<212> TYPE: DNA
<213> ORGANISM: Artificial
<220> FEATURE:
<223> OTHER INFORMATION: Probe

<400> SEQUENCE: 7

| | |
|---|---|
| ggtttcggcc gttcatt | 17 |

<210> SEQ ID NO 8
<211> LENGTH: 16
<212> TYPE: DNA
<213> ORGANISM: Artificial
<220> FEATURE:
<223> OTHER INFORMATION: Probe

<400> SEQUENCE: 8

| | |
|---|---|
| gtttcggccg ttcatt | 16 |

<210> SEQ ID NO 9
<211> LENGTH: 16
<212> TYPE: DNA
<213> ORGANISM: Artificial
<220> FEATURE:
<223> OTHER INFORMATION: Probe

<400> SEQUENCE: 9

| | |
|---|---|
| ggtttcggcc gttcat | 16 |

<210> SEQ ID NO 10
<211> LENGTH: 17
<212> TYPE: DNA
<213> ORGANISM: Artificial

```
<220> FEATURE:
<223> OTHER INFORMATION: Probe

<400> SEQUENCE: 10
acacgagggt gttttct                                                    17

<210> SEQ ID NO 11
<211> LENGTH: 16
<212> TYPE: DNA
<213> ORGANISM: Artificial
<220> FEATURE:
<223> OTHER INFORMATION: Probe

<400> SEQUENCE: 11
cacgagggtg ttttct                                                     16

<210> SEQ ID NO 12
<211> LENGTH: 16
<212> TYPE: DNA
<213> ORGANISM: Artificial
<220> FEATURE:
<223> OTHER INFORMATION: Probe

<400> SEQUENCE: 12
acacgagggt gttttc                                                     16

<210> SEQ ID NO 13
<211> LENGTH: 18
<212> TYPE: DNA
<213> ORGANISM: Artificial
<220> FEATURE:
<223> OTHER INFORMATION: Probe

<400> SEQUENCE: 13
ccttctcact atttagtg                                                   18

<210> SEQ ID NO 14
<211> LENGTH: 17
<212> TYPE: DNA
<213> ORGANISM: Artificial
<220> FEATURE:
<223> OTHER INFORMATION: Probe

<400> SEQUENCE: 14
ccttctcact atttagt                                                    17

<210> SEQ ID NO 15
<211> LENGTH: 18
<212> TYPE: DNA
<213> ORGANISM: Artificial
<220> FEATURE:
<223> OTHER INFORMATION: Probe

<400> SEQUENCE: 15
agaaacacat gtatgagg                                                   18

<210> SEQ ID NO 16
<211> LENGTH: 17
<212> TYPE: DNA
<213> ORGANISM: Artificial
<220> FEATURE:
<223> OTHER INFORMATION: Probe

<400> SEQUENCE: 16
gaggaaatta tagggag                                                    17
```

```
<210> SEQ ID NO 17
<211> LENGTH: 18
<212> TYPE: DNA
<213> ORGANISM: Artificial
<220> FEATURE:
<223> OTHER INFORMATION: Probe

<400> SEQUENCE: 17
taaaacacgc aaaatata                                                   18

<210> SEQ ID NO 18
<211> LENGTH: 17
<212> TYPE: DNA
<213> ORGANISM: Artificial
<220> FEATURE:
<223> OTHER INFORMATION: Probe

<400> SEQUENCE: 18
ccatataaaa cacgcaa                                                    17

<210> SEQ ID NO 19
<211> LENGTH: 17
<212> TYPE: DNA
<213> ORGANISM: Artificial
<220> FEATURE:
<223> OTHER INFORMATION: Probe

<400> SEQUENCE: 19
ctcacttctc tggagtg                                                    17

<210> SEQ ID NO 20
<211> LENGTH: 17
<212> TYPE: DNA
<213> ORGANISM: Artificial
<220> FEATURE:
<223> OTHER INFORMATION: Probe

<400> SEQUENCE: 20
ctggagtggt tatgaga                                                    17

<210> SEQ ID NO 21
<211> LENGTH: 17
<212> TYPE: DNA
<213> ORGANISM: Artificial
<220> FEATURE:
<223> OTHER INFORMATION: Probe

<400> SEQUENCE: 21
cggtagtgtt ttcttga                                                    17

<210> SEQ ID NO 22
<211> LENGTH: 19
<212> TYPE: DNA
<213> ORGANISM: Artificial
<220> FEATURE:
<223> OTHER INFORMATION: Probe

<400> SEQUENCE: 22
gcggtagtgt tttcttgaa                                                  19

<210> SEQ ID NO 23
<211> LENGTH: 15
<212> TYPE: DNA
<213> ORGANISM: Artificial
<220> FEATURE:
<223> OTHER INFORMATION: Probe
```

```
<400> SEQUENCE: 23
acaaggtttc ggccg                                                      15

<210> SEQ ID NO 24
<211> LENGTH: 14
<212> TYPE: DNA
<213> ORGANISM: Artificial
<220> FEATURE:
<223> OTHER INFORMATION: Probe

<400> SEQUENCE: 24
acaaggtttc ggcc                                                       14

<210> SEQ ID NO 25
<211> LENGTH: 13
<212> TYPE: DNA
<213> ORGANISM: Artificial
<220> FEATURE:
<223> OTHER INFORMATION: Probe

<400> SEQUENCE: 25
acaaggtttc ggc                                                        13

<210> SEQ ID NO 26
<211> LENGTH: 12
<212> TYPE: DNA
<213> ORGANISM: Artificial
<220> FEATURE:
<223> OTHER INFORMATION: Probe

<400> SEQUENCE: 26
acaaggtttc gg                                                         12

<210> SEQ ID NO 27
<211> LENGTH: 17
<212> TYPE: DNA
<213> ORGANISM: Artificial
<220> FEATURE:
<223> OTHER INFORMATION: Probe

<400> SEQUENCE: 27
gggagtatac tgggagg                                                    17

<210> SEQ ID NO 28
<211> LENGTH: 17
<212> TYPE: DNA
<213> ORGANISM: Artificial
<220> FEATURE:
<223> OTHER INFORMATION: Probe

<400> SEQUENCE: 28
cggtggggag tatactg                                                    17

<210> SEQ ID NO 29
<211> LENGTH: 16
<212> TYPE: DNA
<213> ORGANISM: Artificial
<220> FEATURE:
<223> OTHER INFORMATION: Probe

<400> SEQUENCE: 29
gggagtatac tgggag                                                     16

<210> SEQ ID NO 30
```

```
<211> LENGTH: 17
<212> TYPE: DNA
<213> ORGANISM: Artificial
<220> FEATURE:
<223> OTHER INFORMATION: Probe

<400> SEQUENCE: 30
tattccaaac ggtgaga                                                    17

<210> SEQ ID NO 31
<211> LENGTH: 18
<212> TYPE: DNA
<213> ORGANISM: Artificial
<220> FEATURE:
<223> OTHER INFORMATION: Probe

<400> SEQUENCE: 31
gtgagagatt tctgtgct                                                   18

<210> SEQ ID NO 32
<211> LENGTH: 17
<212> TYPE: DNA
<213> ORGANISM: Artificial
<220> FEATURE:
<223> OTHER INFORMATION: Probe

<400> SEQUENCE: 32
tgtggagttt tcatatc                                                    17

<210> SEQ ID NO 33
<211> LENGTH: 17
<212> TYPE: DNA
<213> ORGANISM: Artificial
<220> FEATURE:
<223> OTHER INFORMATION: Probe

<400> SEQUENCE: 33
tttcatatct ttgcaac                                                    17

<210> SEQ ID NO 34
<211> LENGTH: 16
<212> TYPE: DNA
<213> ORGANISM: Artificial
<220> FEATURE:
<223> OTHER INFORMATION: Probe

<400> SEQUENCE: 34
tttgggcatt cgagca                                                     16

<210> SEQ ID NO 35
<211> LENGTH: 15
<212> TYPE: DNA
<213> ORGANISM: Artificial
<220> FEATURE:
<223> OTHER INFORMATION: Probe

<400> SEQUENCE: 35
ctttgggcat tcgag                                                      15

<210> SEQ ID NO 36
<211> LENGTH: 13
<212> TYPE: DNA
<213> ORGANISM: Artificial
<220> FEATURE:
<223> OTHER INFORMATION: Probe

<400> SEQUENCE: 36
```
gggcattcga gca                                              13

<210> SEQ ID NO 37
<211> LENGTH: 15
<212> TYPE: DNA
<213> ORGANISM: Artificial
<220> FEATURE:
<223> OTHER INFORMATION: Probe

<400> SEQUENCE: 37
gcattcgagc aatcg                                            15

<210> SEQ ID NO 38
<211> LENGTH: 15
<212> TYPE: DNA
<213> ORGANISM: Artificial
<220> FEATURE:
<223> OTHER INFORMATION: Probe

<400> SEQUENCE: 38
ggcattcgag caatc                                            15

<210> SEQ ID NO 39
<211> LENGTH: 17
<212> TYPE: DNA
<213> ORGANISM: Artificial
<220> FEATURE:
<223> OTHER INFORMATION: Probe

<400> SEQUENCE: 39
acacactgtg gagtttt                                          17

<210> SEQ ID NO 40
<211> LENGTH: 17
<212> TYPE: DNA
<213> ORGANISM: Artificial
<220> FEATURE:
<223> OTHER INFORMATION: Probe

<400> SEQUENCE: 40
aaaaccgttt caataca                                          17

<210> SEQ ID NO 41
<211> LENGTH: 17
<212> TYPE: DNA
<213> ORGANISM: Artificial
<220> FEATURE:
<223> OTHER INFORMATION: Probe

<400> SEQUENCE: 41 gcaactttt ctttggg                                           17

<210> SEQ ID NO 42
<211> LENGTH: 18
<212> TYPE: DNA
<213> ORGANISM: Artificial
<220> FEATURE:
<223> OTHER INFORMATION: Probe

<400> SEQUENCE: 42
tcattaaatt tttgtcaa                                         18

<210> SEQ ID NO 43
<211> LENGTH: 18
<212> TYPE: DNA

-continued

<213> ORGANISM: Artificial
<220> FEATURE:
<223> OTHER INFORMATION: Probe

<400> SEQUENCE: 43
gtcaaaaaca agaatttt                                                       18

<210> SEQ ID NO 44
<211> LENGTH: 17
<212> TYPE: DNA
<213> ORGANISM: Artificial
<220> FEATURE:
<223> OTHER INFORMATION: Probe

<400> SEQUENCE: 44
acacacattg tctagtt                                                        17

<210> SEQ ID NO 45
<211> LENGTH: 17
<212> TYPE: DNA
<213> ORGANISM: Artificial
<220> FEATURE:
<223> OTHER INFORMATION: Probe

<400> SEQUENCE: 45
tattgactta gcaagag                                                        17

<210> SEQ ID NO 46
<211> LENGTH: 17
<212> TYPE: DNA
<213> ORGANISM: Artificial
<220> FEATURE:
<223> OTHER INFORMATION: Probe

<400> SEQUENCE: 46
ctaataagca gtctttc                                                        17

<210> SEQ ID NO 47
<211> LENGTH: 19
<212> TYPE: DNA
<213> ORGANISM: Artificial
<220> FEATURE:
<223> OTHER INFORMATION: Probe

<400> SEQUENCE: 47
cagtctttct gaaataatg                                                      19

<210> SEQ ID NO 48
<211> LENGTH: 18
<212> TYPE: DNA
<213> ORGANISM: Artificial
<220> FEATURE:
<223> OTHER INFORMATION: Probe

<400> SEQUENCE: 48
ctaataagca gtctttct                                                       18

<210> SEQ ID NO 49
<211> LENGTH: 17
<212> TYPE: DNA
<213> ORGANISM: Artificial
<220> FEATURE:
<223> OTHER INFORMATION: Probe

<400> SEQUENCE: 49
gttaaaacct ttaacca                                                        17

<210> SEQ ID NO 50
<211> LENGTH: 17
<212> TYPE: DNA
<213> ORGANISM: Artificial
<220> FEATURE:
<223> OTHER INFORMATION: Probe

<400> SEQUENCE: 50
taggcaggtt tagaagt                                                  17

<210> SEQ ID NO 51
<211> LENGTH: 16
<212> TYPE: DNA
<213> ORGANISM: Artificial
<220> FEATURE:
<223> OTHER INFORMATION: Probe

<400> SEQUENCE: 51
atatcagcta ggcagg                                                   16

<210> SEQ ID NO 52
<211> LENGTH: 17
<212> TYPE: DNA
<213> ORGANISM: Artificial
<220> FEATURE:
<223> OTHER INFORMATION: Probe

<400> SEQUENCE: 52
ggctcggctt aacaaca                                                  17

<210> SEQ ID NO 53
<211> LENGTH: 22
<212> TYPE: DNA
<213> ORGANISM: Artificial
<220> FEATURE:
<223> OTHER INFORMATION: Probe

<400> SEQUENCE: 53
agatctttta caataatgtg ta                                            22

<210> SEQ ID NO 54
<211> LENGTH: 18
<212> TYPE: DNA
<213> ORGANISM: Artificial
<220> FEATURE:
<223> OTHER INFORMATION: Probe

<400> SEQUENCE: 54
cgaaaggttc aaggcaaa                                                 18

<210> SEQ ID NO 55
<211> LENGTH: 17
<212> TYPE: DNA
<213> ORGANISM: Artificial
<220> FEATURE:
<223> OTHER INFORMATION: Probe

<400> SEQUENCE: 55
cgttttactt tacaagg                                                  17

<210> SEQ ID NO 56
<211> LENGTH: 17
<212> TYPE: DNA
<213> ORGANISM: Artificial
<220> FEATURE:

<223> OTHER INFORMATION: Probe

<400> SEQUENCE: 56
aggcaaaggg ttgcttt                17

<210> SEQ ID NO 57
<211> LENGTH: 18
<212> TYPE: DNA
<213> ORGANISM: Artificial
<220> FEATURE:
<223> OTHER INFORMATION: Probe

<400> SEQUENCE: 57
ccaacaccac actgtgtg               18

<210> SEQ ID NO 58
<211> LENGTH: 17
<212> TYPE: DNA
<213> ORGANISM: Artificial
<220> FEATURE:
<223> OTHER INFORMATION: Probe

<400> SEQUENCE: 58
cacacgtcaa caaaaga                17

<210> SEQ ID NO 59
<211> LENGTH: 20
<212> TYPE: DNA
<213> ORGANISM: Artificial
<220> FEATURE:
<223> OTHER INFORMATION: Probe

<400> SEQUENCE: 59
gtcaacaaaa gatctaaaag             20

<210> SEQ ID NO 60
<211> LENGTH: 16
<212> TYPE: DNA
<213> ORGANISM: Artificial
<220> FEATURE:
<223> OTHER INFORMATION: Probe

<400> SEQUENCE: 60
tgcgcagagc tggccg                 16

<210> SEQ ID NO 61
<211> LENGTH: 17
<212> TYPE: DNA
<213> ORGANISM: Artificial
<220> FEATURE:
<223> OTHER INFORMATION: Probe

<400> SEQUENCE: 61
aaacgttgcg gacgaag                17

<210> SEQ ID NO 62
<211> LENGTH: 15
<212> TYPE: DNA
<213> ORGANISM: Artificial
<220> FEATURE:
<223> OTHER INFORMATION: Probe

<400> SEQUENCE: 62
acgttgcgga cgaag                  15

<210> SEQ ID NO 63
<211> LENGTH: 17
<212> TYPE: DNA
<213> ORGANISM: Artificial
<220> FEATURE:
<223> OTHER INFORMATION: Probe

<400> SEQUENCE: 63
gccgaaaaga aacgttg                                                        17

<210> SEQ ID NO 64
<211> LENGTH: 17
<212> TYPE: DNA
<213> ORGANISM: Artificial
<220> FEATURE:
<223> OTHER INFORMATION: Probe

<400> SEQUENCE: 64
tacatcggga cgctttg                                                        17

<210> SEQ ID NO 65
<211> LENGTH: 20
<212> TYPE: DNA
<213> ORGANISM: Artificial
<220> FEATURE:
<223> OTHER INFORMATION: Probe

<400> SEQUENCE: 65
cctaatcggc ttagcgtagg                                                     20

<210> SEQ ID NO 66
<211> LENGTH: 22
<212> TYPE: DNA
<213> ORGANISM: Artificial
<220> FEATURE:
<223> OTHER INFORMATION: Primer

<400> SEQUENCE: 66
ttgattacgt ccctgccctt tg                                                  22

<210> SEQ ID NO 67
<211> LENGTH: 20
<212> TYPE: DNA
<213> ORGANISM: Artificial
<220> FEATURE:
<223> OTHER INFORMATION: Primer

<400> SEQUENCE: 67
gatatgctta agttcagcgg                                                     20

<210> SEQ ID NO 68
<211> LENGTH: 99
<212> TYPE: DNA
<213> ORGANISM: Artificial
<220> FEATURE:
<223> OTHER INFORMATION: Probe

<400> SEQUENCE: 68
ttgattacgt ccctgccctt tggacgaacg ctggccctac ctaatcgcga tagcgtagga         60
gccacggcta actacgtgcc cgctgaactt aagcatatc                                99

<210> SEQ ID NO 69
<211> LENGTH: 20
<212> TYPE: DNA
<213> ORGANISM: Artificial
<220> FEATURE:

-continued

```
<223> OTHER INFORMATION: Probe

<400> SEQUENCE: 69
cctaatcgcg atagcgtagg                                                   20
```